US010517950B1

(12) United States Patent
Tabuteau

(10) Patent No.: US 10,517,950 B1
(45) Date of Patent: *Dec. 31, 2019

(54) PHARMACEUTICAL COMPOSITIONS COMPRISING MELOXICAM

(71) Applicant: AXSOME THERAPEUTICS, INC., New York, NY (US)

(72) Inventor: Herriot Tabuteau, New York, NY (US)

(73) Assignee: AXSOME THERAPEUTICS, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/567,859

(22) Filed: Sep. 11, 2019

Related U.S. Application Data

(63) Continuation-in-part of application No. 16/006,548, filed on Jun. 12, 2018, now Pat. No. 10,463,736, which is a continuation of application No. 15/902,770, filed on Feb. 22, 2018, now Pat. No. 10,029,010, which is a continuation of application No. 15/797,955, filed on Oct. 30, 2017, now Pat. No. 10,058,614, which is a continuation-in-part of application No. 15/132,130, filed on Apr. 18, 2016, now Pat. No. 9,821,075, which is a continuation of application No. PCT/US2016/026991, filed on Apr. 11, 2016.

(60) Provisional application No. 62/114,215, filed on Feb. 10, 2015, provisional application No. 62/259,993, filed on Nov. 25, 2015, provisional application No. 62/526,884, filed on Jun. 29, 2017, provisional application No. 62/536,466, filed on Jul. 25, 2017.

(51) Int. Cl.
| | | |
|---|---|---|
| A61K 47/02 | (2006.01) | |
| A61K 31/5415 | (2006.01) | |
| A61K 31/4439 | (2006.01) | |
| A61K 9/00 | (2006.01) | |
| A61K 45/06 | (2006.01) | |
| A61K 47/40 | (2006.01) | |
| A61K 9/20 | (2006.01) | |
| A61K 47/69 | (2017.01) | |
| C08B 37/16 | (2006.01) | |

(52) U.S. Cl.
CPC ............ *A61K 47/02* (2013.01); *A61K 9/0053* (2013.01); *A61K 9/2009* (2013.01); *A61K 31/4439* (2013.01); *A61K 31/5415* (2013.01); *A61K 45/06* (2013.01); *A61K 47/40* (2013.01); *A61K 47/6951* (2017.08); *C08B 37/0012* (2013.01); *C08B 37/0015* (2013.01)

(58) Field of Classification Search
None
See application file for complete search history.

(56) References Cited

U.S. PATENT DOCUMENTS

| | | |
|---|---|---|
| 5,872,145 A | 2/1999 | Plachetka |
| 6,060,499 A | 5/2000 | Plachetka |
| 6,077,539 A | 6/2000 | Plachetka et al. |
| 6,284,269 B1 * | 9/2001 | Struengmann ..... A61K 47/6951 424/461 |
| 6,384,034 B2 | 5/2002 | Simitchieva et al. |
| 6,479,551 B1 | 11/2002 | Plachetka et al. |
| 6,495,535 B1 | 12/2002 | Plachetka et al. |
| 6,586,458 B1 | 7/2003 | Plachetka |
| 6,926,907 B2 | 8/2005 | Plachetka |
| 7,030,162 B2 | 4/2006 | Plachetka et al. |
| 7,060,694 B2 | 6/2006 | Plachetka et al. |
| 7,332,183 B2 | 2/2008 | Plachetka et al. |
| 8,022,095 B2 | 9/2011 | Plachetka |
| 8,206,741 B2 | 6/2012 | Plachetka |

(Continued)

FOREIGN PATENT DOCUMENTS

| | | |
|---|---|---|
| CA | 2565941 A1 | 11/2005 |
| CN | 101987081 | 3/2011 |

(Continued)

OTHER PUBLICATIONS

Meloxicam' at http://web.archive.org/web/20141113013539/ https://www.mayoclinic.org/drugs-supplements/meloxicam-oral-route/proper-use/drg-20066928 (Year: 2014).*
Lainez, M. in Neuropsychiatric Disease and Treatment, 2(3) 247-259 (2006) (Year: 2006).*
Hu et al., Predicting Biological Functions of Compounds Based on Chemical-Chemical Interactions, PLoS One, 6(12), Dec. 2011, 9 pgs.
Johnell et al., Concomitant Use of Gastroprotective Drugs Among Elderly NSAID/COX-2 Selective Inhibitor Users: A Nationwide Register-Based Study, Clinical Drug Investigation, 28(11), 687-695, Nov. 2008.

(Continued)

*Primary Examiner* — Dennis Heyer
(74) *Attorney, Agent, or Firm* — Maschoff Brennan; Brent A. Johnson; Yuefen Zhou

(57) ABSTRACT

Disclosed herein are compositions comprising an NSAID such as meloxicam and/or rizatriptan in combination with a cyclodextrin and/or a carbonate or a bicarbonate. These compositions may be orally administered, for example, to improve the bioavailability or pharmacokinetics of the NSAID for the treatment of pain such as migraine, arthritis, and other conditions. Also disclosed herein are methods of treating pain, such as migraine, comprising administering meloxicam and rizatriptan to a human being suffering from pain, such as migraine. For migraine, these methods may be particularly useful when the meloxicam and rizatriptan are administered while the human being is suffering from an acute attack of migraine pain or migraine aura. In some embodiments, the combination of meloxicam and rizatriptan may be administered in a manner that results in a $T_{max}$ of meloxicam of 3 hours or less.

25 Claims, 6 Drawing Sheets

(56) References Cited

U.S. PATENT DOCUMENTS

| | | | |
|---|---|---|---|
| 8,512,727 B2* | 8/2013 | Cooper | A61K 9/145 424/422 |
| 8,557,285 B2 | 10/2013 | Plachetka | |
| 8,835,407 B2 | 9/2014 | Mosher et al. | |
| 8,852,636 B2 | 10/2014 | Plachetka | |
| 8,858,996 B2 | 10/2014 | Plachetka | |
| 8,865,190 B2 | 10/2014 | Plachetka | |
| 8,945,621 B2 | 2/2015 | Ault et al. | |
| 9,161,920 B2 | 10/2015 | Plachetka | |
| 9,198,888 B2 | 12/2015 | Plachetka | |
| 9,220,698 B2 | 12/2015 | Ault et al. | |
| 9,265,732 B2 | 2/2016 | Plachetka et al. | |
| 9,345,695 B2 | 5/2016 | Plachetka | |
| 9,364,439 B2 | 6/2016 | Plachetka | |
| 9,393,208 B2 | 7/2016 | Ault et al. | |
| 9,539,214 B2 | 1/2017 | Plachetka | |
| 9,707,181 B2 | 7/2017 | Plachetka | |
| 9,801,824 B2 | 10/2017 | Ault et al. | |
| 9,801,827 B2 | 10/2017 | Plachetka et al. | |
| 9,821,075 B2 | 11/2017 | Tabuteau | |
| 10,029,010 B1 | 7/2018 | Tabuteau | |
| 10,058,614 B2 | 8/2018 | Tabuteau | |
| 10,137,131 B2 | 11/2018 | Tabuteau | |
| 10,195,278 B2 | 2/2019 | Tabuteau | |
| 10,195,279 B2 | 2/2019 | Tabuteau | |
| 10,265,324 B2 | 4/2019 | Tabuteau | |
| 10,265,399 B2 | 4/2019 | Tabuteau | |
| 10,265,400 B2 | 4/2019 | Tabuteau | |
| 10,307,484 B2 | 6/2019 | Tabuteau | |
| 10,322,181 B2 | 6/2019 | Tabuteau | |
| 10,363,312 B2 | 7/2019 | Tabuteau | |
| 10,369,224 B2 | 8/2019 | Tabuteau | |
| 10,369,225 B2 | 8/2019 | Tabuteau | |
| 10,426,839 B2 | 10/2019 | Tabuteau | |
| 2002/0016348 A1 | 2/2002 | Simitchieva et al. | |
| 2004/0229038 A1 | 11/2004 | Cooper et al. | |
| 2007/0281927 A1 | 12/2007 | Tyavanagimatt et al. | |
| 2009/0068262 A1 | 3/2009 | Zalit et al. | |
| 2009/0203680 A1 | 8/2009 | Hanna et al. | |
| 2010/0226943 A1 | 9/2010 | Brennan et al. | |
| 2013/0266658 A1 | 10/2013 | Weiß et al. | |
| 2016/0228576 A1 | 8/2016 | Tabuteau | |
| 2018/0050106 A1 | 2/2018 | Tabuteau | |
| 2018/0207274 A1 | 7/2018 | Tabuteau | |
| 2018/0214380 A1 | 8/2018 | Tabuteau | |
| 2018/0256593 A1 | 9/2018 | Tabuteau | |
| 2018/0264114 A1 | 9/2018 | Tabuteau | |
| 2018/0264115 A1 | 9/2018 | Tabuteau | |
| 2018/0271981 A1 | 9/2018 | Tabuteau | |
| 2018/0280306 A1 | 10/2018 | Tabuteau | |
| 2018/0280308 A1 | 10/2018 | Tabuteau | |
| 2018/0280512 A1 | 10/2018 | Tabuteau | |
| 2018/0289806 A1 | 10/2018 | Tabuteau | |
| 2018/0289807 A1 | 10/2018 | Tabuteau | |
| 2018/0289808 A1 | 10/2018 | Tabuteau | |
| 2019/0000975 A1 | 1/2019 | Tabuteau | |
| 2019/0070192 A1 | 3/2019 | Tabuteau | |
| 2019/0142942 A1 | 5/2019 | Tabuteau | |
| 2019/0142943 A1 | 5/2019 | Tabuteau | |
| 2019/0224320 A1 | 7/2019 | Tabuteau | |
| 2019/0224321 A1 | 7/2019 | Tabuteau | |
| 2019/0231792 A1 | 8/2019 | Tabuteau | |
| 2019/0255177 A1 | 8/2019 | Tabuteau | |
| 2019/0307884 A1 | 10/2019 | Tabuteau | |
| 2019/0314504 A1 | 10/2019 | Tabuteau | |

FOREIGN PATENT DOCUMENTS

| | | |
|---|---|---|
| CN | 102526058 A | 7/2012 |
| WO | 2000035448 | 6/2000 |
| WO | 2000059475 | 10/2000 |
| WO | 2005076987 | 8/2005 |
| WO | 2005105102 A1 | 11/2005 |
| WO | 2008006216 | 1/2008 |
| WO | 2012072570 | 6/2012 |
| WO | 2014161131 A1 | 10/2014 |
| WO | 2016131067 | 8/2016 |
| WO | 2017042607 | 3/2017 |
| WO | 2018129220 | 7/2018 |

OTHER PUBLICATIONS

Leonard et al., Proton Pump Inhibitors and Traditional Nonsteroidal Anti-Inflammatory Drugs and the Risk of Acute Interstitial Nephritis and Acute Kidney Injury, Pharmacoepidemiology and Drug Safety, 21(11), 1155-1172, Nov. 2012.

Vonkeman et al., Proton-Pump Inhibitors are Associated with a Reduced Risk for Bleeding and Perforated Gastroduodenal Ulcers Attributable to Non-Steroidal Anti-Inflammatory Drugs: A Nested Case-Control Study, Arthritis Research & Therapy, 9(3), May 2007, 8 pgs.

Yilmaz et al., Does Adding Misoprostol to Standard Intravenous Proton Pump Inhibitor Protocol Improve the Outcome of Aspirin/NSAID-Induced Upper Gastrointestinal Bleeding?, Digestive Diseases and Sciences, 52(1), 110-118, Jan. 2007.

International search report dated Aug. 11, 2016, corresponding to international patent application No. PCT/ US2016/026991.

Written opinion of the international searching authority dated Aug. 11, 2016, corresponding to international patent application No. PCT/US2016/026991.

Stella et al., Toxicologic Pathology, 2008, 36:30-42.

Jain et al., AAAPS PharmSciTech, 2011, 12(4):1163-1175.

Baboota et al., Journal of Inclusion Phenomena and Macrocyclic Chemistry, 2005, 51:219-224.

U.S. Appl. No. 15/132,130, filed Apr. 18, 2016 First Named Inventor: Herriot Tabuteau Assignee: Axsome Therapeutics, Inc.

U.S. Appl. No. 15/797,955, filed Oct. 30, 2017 First Named Inventor: Herriot Tabuteau Assignee: Axsome Therapeutics, Inc.

U.S. Appl. No. 15/902,770, filed Feb. 22, 2018 First Named Inventor: Herriot Tabuteau Assignee: Axsome Therapeutics, Inc.

U.S. Appl. No. 15/936,176, filed Mar. 26, 2018 First Names Inventor: Herriot Tabuteau Assignee: Axsome Therapeutics, Inc.

U.S. Appl. No. 15/976,800, filed May 10, 2018 First Named Inventor: Herriot Tabuteau Assingee: Axsome Therapeutics, Inc.

U.S. Appl. No. 15/984,055, filed May 18, 2018 First Named Inventor: Herriot Tabuteau Assignee: Axsome Therapeutics, Inc.

U.S. Appl. No. 15/986,215, filed May 22, 2018 First Named Inventor: Herriot Tabuteau Assignee: Axsome Therapeutics, Inc.

U.S. Appl. No. 15/988,104, filed May 24, 2018 First Named Inventor: Herriot Tabuteau Assignee: Axsome Therapeutics, Inc.

U.S. Appl. No. 15/989,734, filed May 25, 2018 First Named Inventor: Herriot Tabuteau Assignee: Axsome Therapeutics, Inc.

U.S. Appl. No. 16/000,701, filed Jun. 5, 2018 First Named Inventor: Herriot Tabuteau Assignee: Axsome Therapeutics, Inc.

U.S. Appl. No. 16/001,697, filed Jun. 6, 2018 First Named Inventor: Herriot Tabuteau Assignee: Axsome Therapeutics, Inc.

U.S. Appl. No. 16/002,865, filed Jun. 7, 2018 First Named Inventor: Herriot Tabuteau Assignee: Axsome Therapeutics, Inc.

U.S. Appl. No. 16/006,548, filed Jun. 12, 2018 First Named Inventor: Herriot Tabuteau Assignee: Axsome Therapeutics, Inc.

U.S. Appl. No. 16/006,642, filed Jun. 12, 2018 First Named Inventor: Herriot Tabuteau Assignee: Axsome Therapeutics, Inc.

U.S. Appl. No. 16/006,692, filed Jun. 12, 2018 First Named Inventor: Herriot Tabuteau Assignee: Axsome Therapeutics, Inc.

Hosie et al., British Journal of Rheumatology, 35 (suppl.1), 39-43, 1996.

Wojtulewski et al., British Journal of Rheumatology; 35 (suppl.1), 22-28, 1996.

Goldstein et al., Intragastric Acid Control in Non-Steroidal Anti-inflammatory Drug Users: Comparison of Esomeprazole, Lansoprazole and Pantoprazole, Alimentary Pharmacology & Therapeutics 23, 1189-1196, 2006.

Euller-Ziegler et al. Meloxicam: a review of its pharmacokinetics, efficacy and tolerability following intramuscular administration, Inflamm. res. 50, Supplement 1, S5-S9, 2001.

U.S. Appl. No. 16/181,086, filed Nov. 5, 2018 First Named Inventor: Herriot Tabuteau Assignee: Axsome Therapeutics, Inc.

(56) References Cited

OTHER PUBLICATIONS

U.S. Appl. No. 16/247,406, filed Jan. 14, 2019 First Named Inventor: Herriot Tabuteau Assignee: Axsome Therapeutics, Inc.
U.S. Appl. No. 16/248,449, filed Jan. 15, 2019 First Named Inventor: Herriot Tabuteau Assignee: Axsome Therapeutics, Inc.
Iroko Pharmaceuticals, Vivlodex Label, Oct. 2015.
Mayo Clinic, http://web.archive.org/web/20141113013539/https://www.mayoclinic.org/drugs-supplements /meloxicam-oral-route/proper-use/drg-20066928 (2014) (retrievd from the internet Mar. 3, 2019) (Year: 2014).
U.S. Appl. No. 16/372,958, filed Apr. 2, 2019 First Named Inventor: Herriot Tabuteau Assignee: Axsome Therapeutics, Inc.
U.S. Appl. No. 16/372,977, filed Apr. 2, 2019 First Named Inventor: Herriot Tabuteau Assignee: Axsome Therapeutics, Inc.
U.S. Appl. No. 16/374,081, filed Apr. 3, 2019 First Named Inventor: Herriot Tabuteau Assignee: Axsome Therapeutics, Inc.
U.S. Appl. No. 16/403,034, filed May 3, 2019 First Named Inventor: Herriot Tabuteau Assignee: Axsome Therapeutics, Inc.
U.S. Appl. No. 16/440,695, filed Jun. 13, 2019 First Named Inventor: Herriot Tabuteau Assignee: Axsome Therapeutics, Inc.
U.S. Appl. No. 16/454,319, filed Jun. 27, 2019 First Named Inventor: Herriot Tabuteau Assignee: Axsome Therapeutics, Inc.
U.S. Appl. No. 16/513,612, filed Jul. 16, 2019 First Named Inventor: Herriot Tabuteau Assignee: Axsome Therapeutics, Inc.
Línez, "Rizatriptan in the treatment of migraine." Neuropsychiatric disease and treatment, 2(3), p. 247, Sep. 2006.
U.S. Appl. No. 16/565,111, filed Sep. 9, 2019 First Named Inventor: Herriot Tabuteau Assignee: Axsome Therapeutics, Inc.
U.S. Appl. No. 16/566,476, filed Sep. 10, 2019 First Named Inventor: Herriot Tabuteau Assignee: Axsome Therapeutics, Inc.
U.S. Appl. No. 16/567,859, filed Sep. 11, 2019 First Named Inventor: Herriot Tabuteau Assignee: Axsome Therapeutics, Inc.
U.S. Appl. No. 16/568,703, filed Sep. 12, 2019 First Named Inventor: Herriot Tabuteau Assignee: Axsome Therapeutics, Inc.
U.S. Appl. No. 16/570,434, filed Sep. 13, 2019 First Named Inventor: Herriot Tabuteau Assignee: Axsome Therapeutics, Inc.
U.S. Appl. No. 16/570,451, filed Sep. 13, 2019 First Named Inventor: Herriot Tabuteau Assignee: Axsome Therapeutics, Inc.
U.S. Appl. No. 16/572,042, filed Sep. 16, 2019 First Named Inventor: Herriot Tabuteau Assignee: Axsome Therapeutics, Inc.
U.S. Appl. No. 16/589,692, filed Oct. 1, 2019 First Named Inventor: Herriot Tabuteau Assignee: Axsome Therapeutics, Inc.
U.S. Appl. No. 16/653,877, filed Oct. 15, 2019, Herriot Tabuteau, Axsome Therapeutics, Inc.
Landy S, Rice K, Lobo B. Central sensitisation and cutaneous allodynia in migraine. CNS drugs, 18(6), 337-42, May 2004.

\* cited by examiner

PHARMACEUTICAL COMPOSITIONS COMPRISING MELOXICAM

CROSS-REFERENCE TO RELATED APPLICATIONS

This application is a continuation-in-part of U.S. patent application Ser. No. 16/006,548, filed Jun. 12, 2018; which is a continuation of U.S. patent application Ser. No. 15/902, 770, filed Feb. 22, 2018, now U.S. Pat. No. 10,029,010; which is a continuation of U.S. patent application Ser. No. 15/797,955, filed Oct. 30, 2017, now U.S. Pat. No. 10,058, 614; which is a continuation-in-part of U.S. patent application Ser. No. 15/132,130, filed Apr. 18, 2016, now U.S. Pat. No. 9,821,075; which is a continuation of International Pat. App. No. PCT/US2016/026991, filed Apr. 11, 2016, which claims the benefit of U.S. Provisional Pat. App. Nos. 62/114, 215, filed Feb. 10, 2015, and 62/259,993, filed Nov. 25, 2015; U.S. patent application Ser. No. 15/797,955 also claims the benefit of U.S. Provisional Pat. App. Nos. 62/526, 884, filed Jun. 29, 2017, and 62/536,466, filed Jul. 25, 2017; all of the above applications are hereby incorporated by reference in their entirety.

BACKGROUND

Meloxicam, which has the structure:

is a nonsteroidal anti-inflammatory (NSAID) drug that exhibits anti-inflammatory, analgesic, and antipyretic activities. The meloxicam mechanism of action may be related to prostaglandin synthetase (cyclo-oxygenase, COX) inhibition which is involved in the initial steps of the arachidonic acid cascade, resulting in the reduced formation of prostaglandins, thromboxanes and prostacylin.

SUMMARY

Meloxicam and some other NSAIDs have poor aqueous solubility which may reduce bioavailability and slow the onset of pain relief resulting from their use. One means of increasing the solubility and bioavailability of meloxicam is through the use of cyclodextrins. Cyclodextrin (also known as cycloamyloses) are generally cyclic polysaccharides which form a bucket-like shape. Cyclodextrins help to increase bioavailability of other molecules because cyclodextrins are hydrophobic on the inside and hydrophilic on the inside which helps to facilitate the transport of molecules. The naturally occurring cyclodextrins include six, seven, and eight glucose units ($\alpha$, $\beta$, and $\gamma$-cyclodextrin, respectively). However, synthetic cyclodextrins containing more or less glucose units are possible. In aqueous solutions, cyclodextrins can form complexes (i.e., an inclusion complex) with drugs by incorporating the drug into the center/ hydrophobic portion of the cyclodextrin ring; although cyclodextrin compounds are also known to aggregate around a drug in a micelle-type structure. This ability of cyclodextrins may allow them to act as carriers to increase the bioavailability of less soluble drugs.

Some embodiments include an inclusion complex of meloxicam in a cyclodextrin.

Some embodiments include a dosage form comprising: 1) an inclusion complex of meloxicam and a cyclodextrin, or 2) meloxicam and a carbonate or a bicarbonate.

Some embodiments include a method of administering meloxicam orally, comprising orally administering a dosage form described herein to a patient in need of treatment.

Some embodiments include a method of administering meloxicam intravenously, comprising intravenously administering a dosage form described herein to a patient in need of treatment.

Disclosed herein are formulations for an inclusion complex of cyclodextrin and meloxicam with bicarbonate and methods of use thereof.

Disclosed herein are formulations and methods for delivering meloxicam with cyclodextrin to a subject by oral, enteral, intravenous, intramuscular, subcutaneous, intranasal, or other parenteral means.

Disclosed also are methods for treating pain and pain associated with conditions by delivering a dosage form with meloxicam, cyclodextrin, and bicarbonate by oral, enteral, intravenous, intramuscular, subcutaneous, intranasal, or other parenteral means to a subject.

A combination of rizatriptan and meloxicam (referred to herein for convenience as a "subject combination") may be used to treat a variety of pain conditions.

Rizatriptan has the structure as shown below.

Rizatriptan

DETAILED DESCRIPTION

Figure 1:
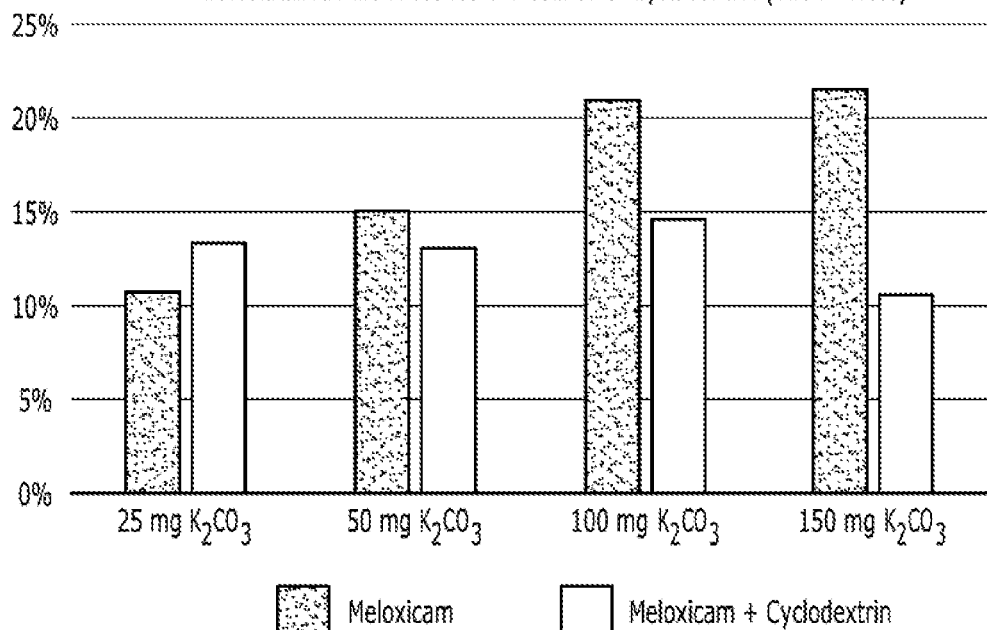
FIG. 1 is a depiction of the results described in Example 2 and contained in Table 6.
Figure 2:
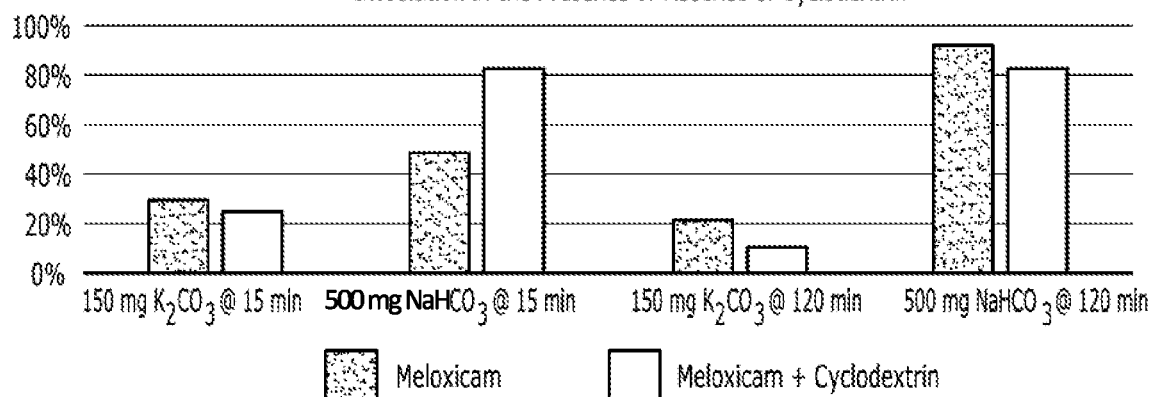
FIG. 2 is another depiction of the results described in Example 2 and contained in Table 6.
Figure 3:
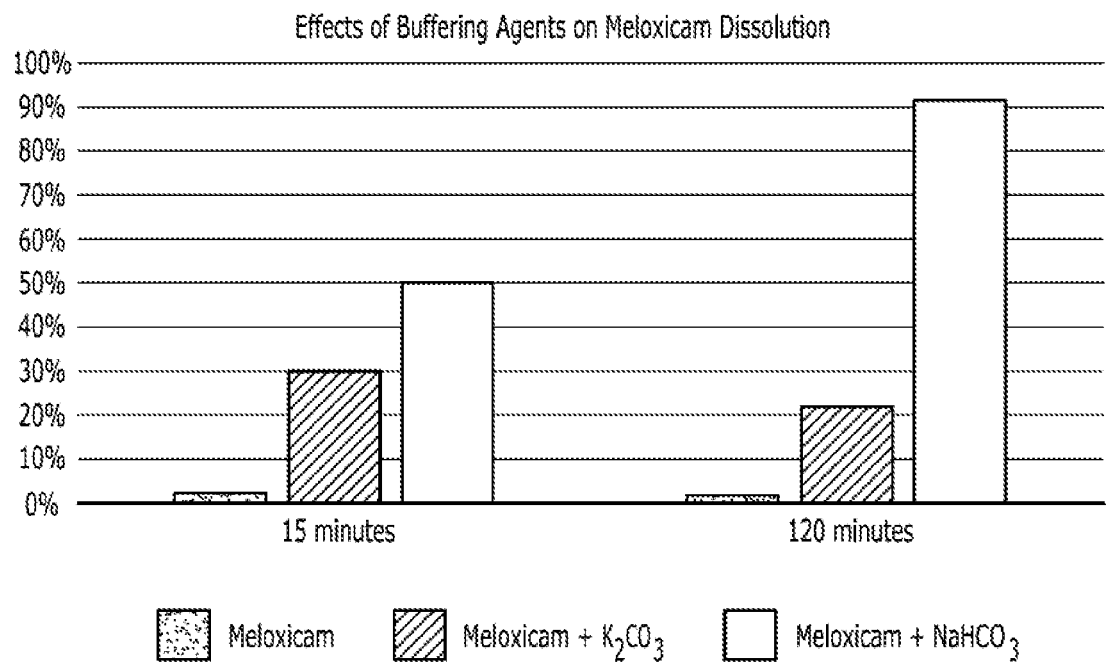
FIG. 3 is another depiction of the results described in Example 2 and contained in Table 6.
Figure 4:
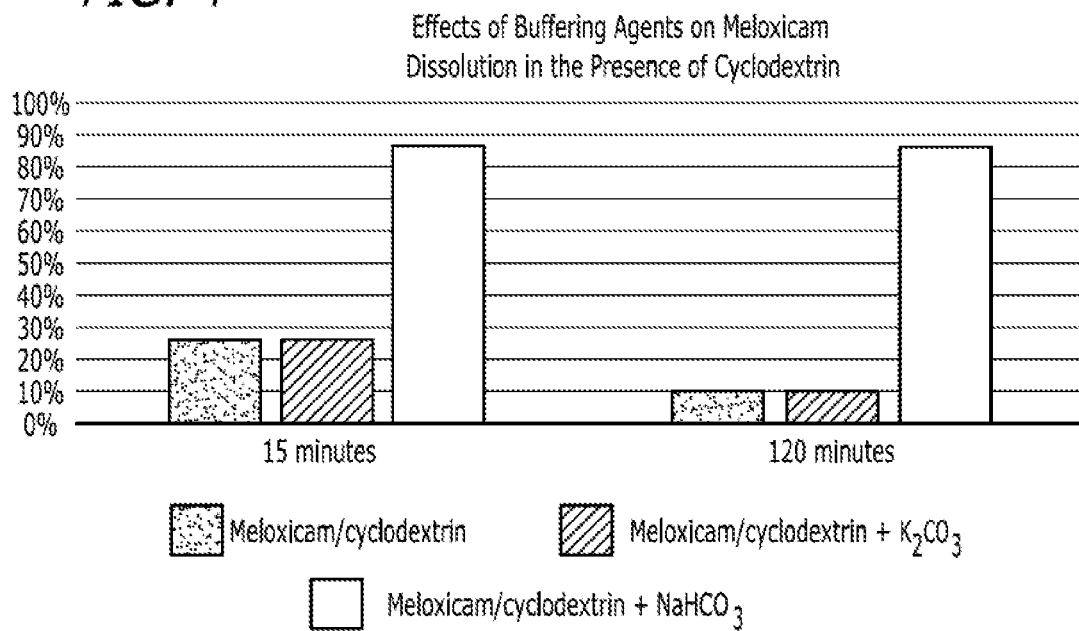
FIG. 4 is another depiction of the results described in Example 2 and contained in Table 6.
Figure 5:
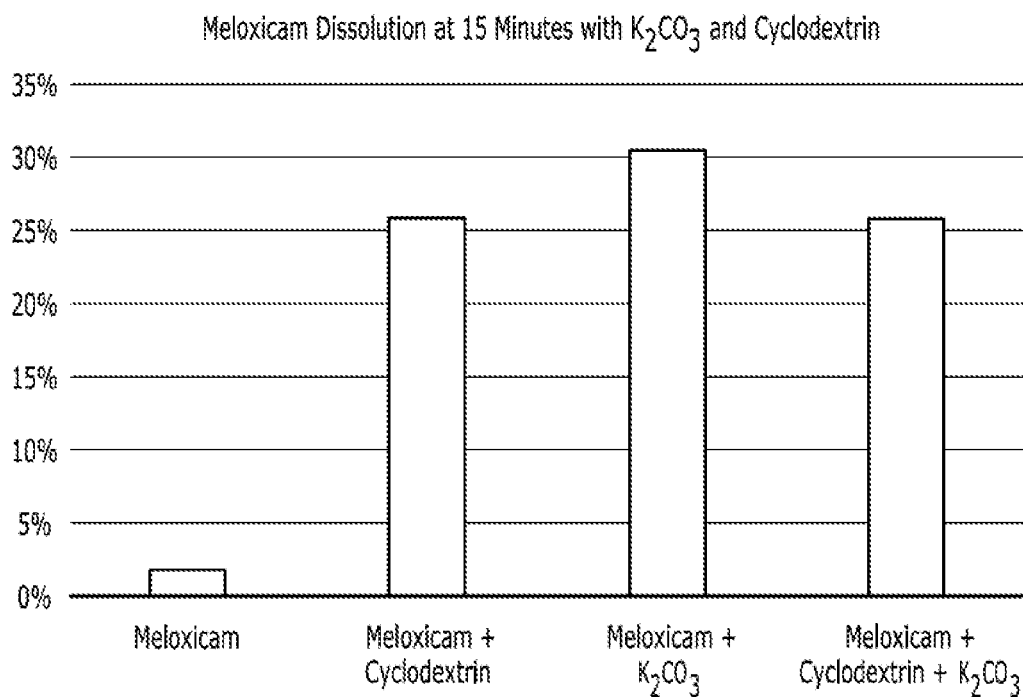
FIG. 5 is another depiction of the results described in Example 2 and contained in Table 6.
Figure 6:
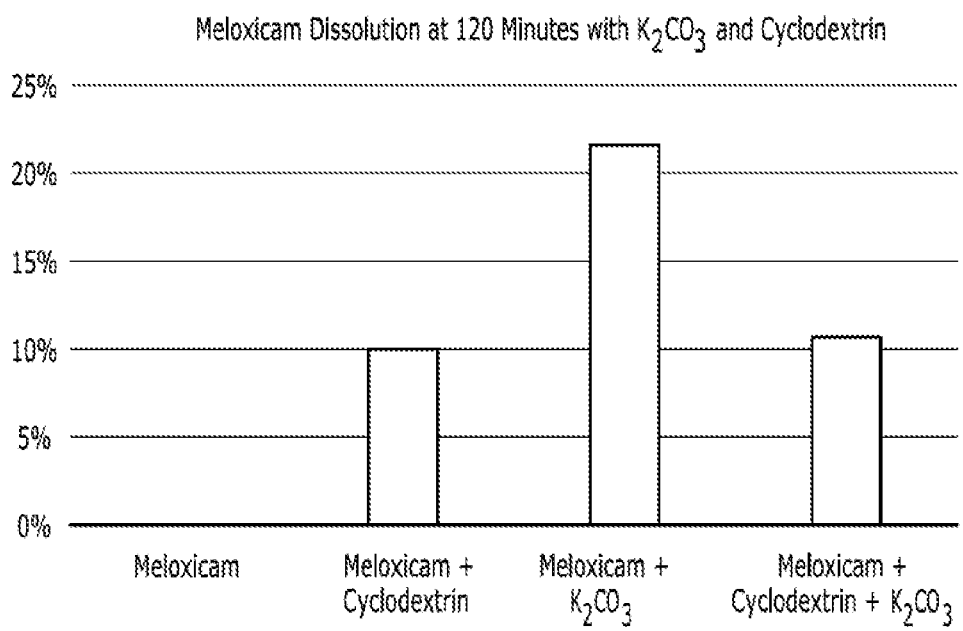
FIG. 6 is another depiction of the results described in Example 2 and contained in Table 6.
Figure 7:
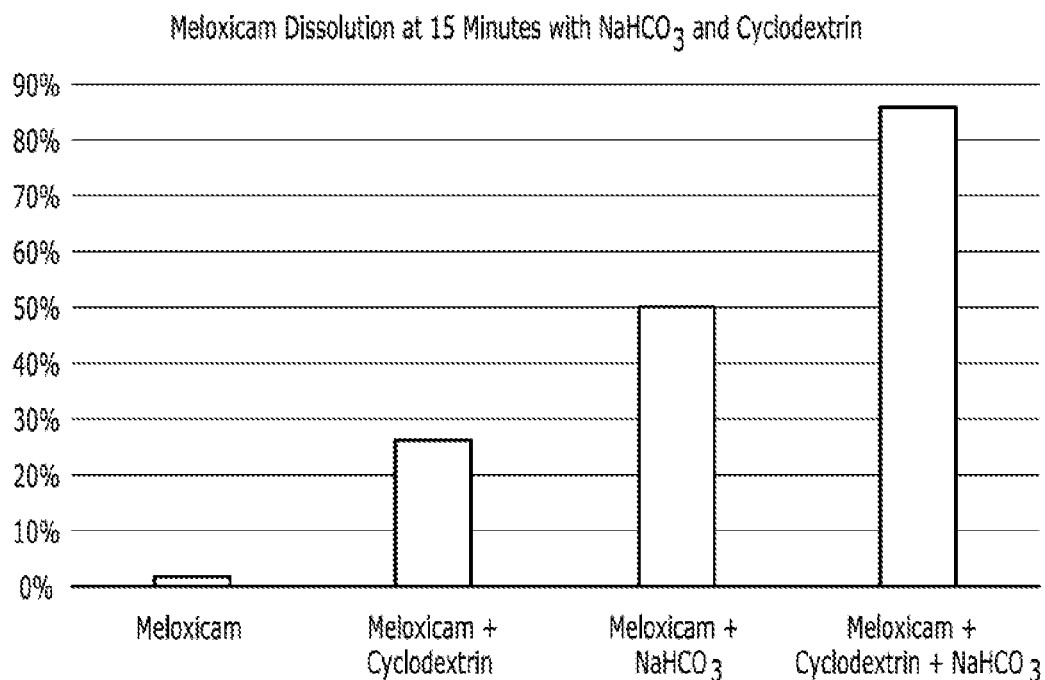
FIG. 7 is another depiction of the results described in Example 2 and contained in Table 6.
Figure 8:
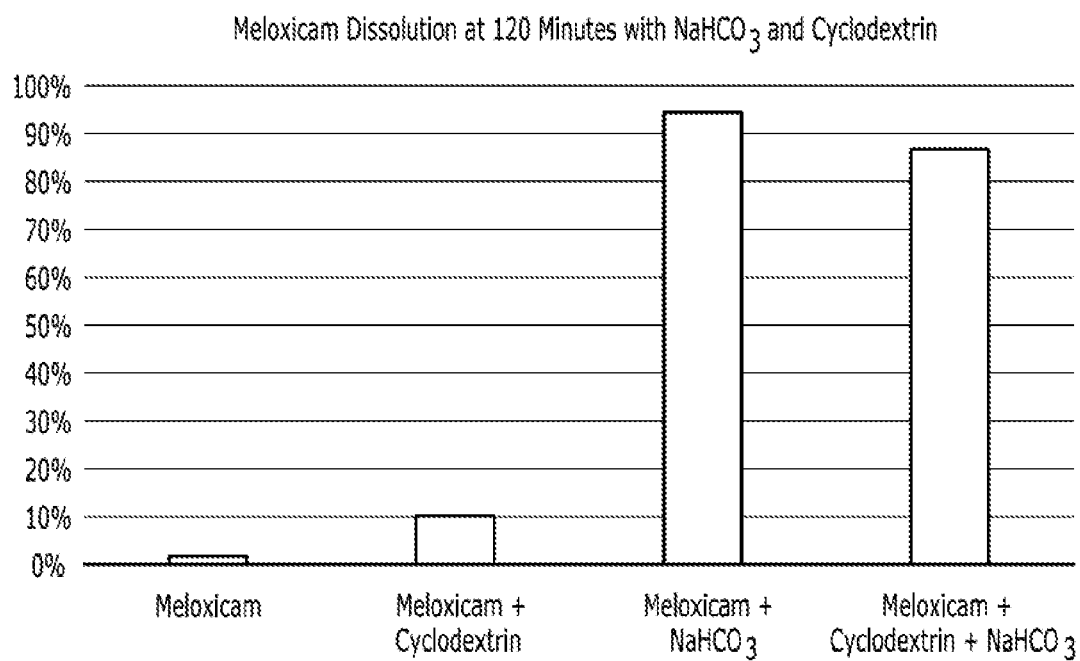
FIG. 8 is another depiction of the results described in Example 2 and contained in Table 6.
Figure 9:
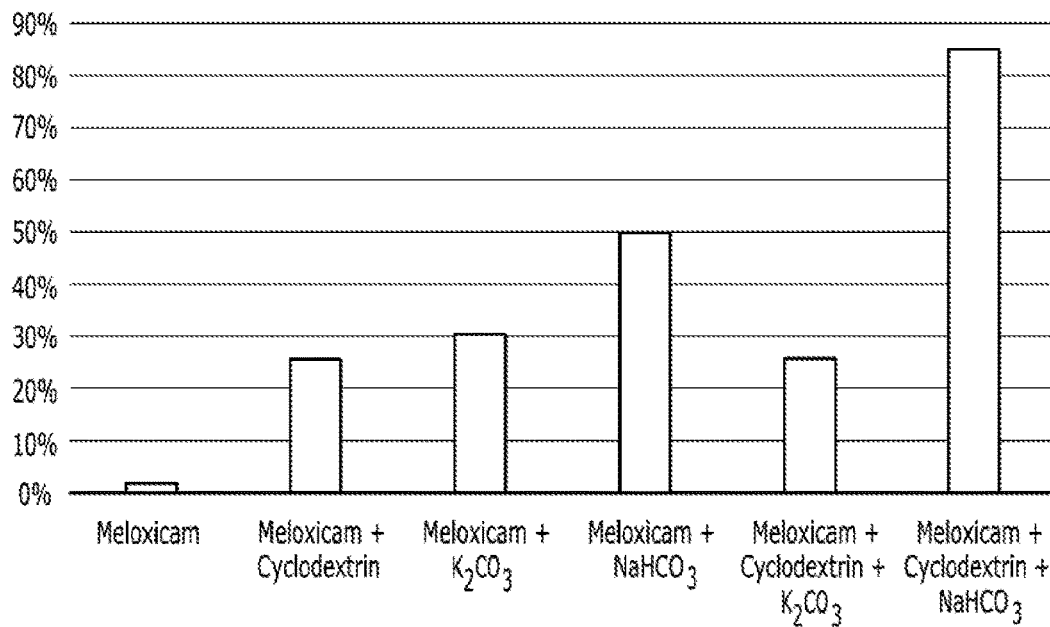
FIG. 9 is another depiction of the results described in Example 2 and contained in Table 6.
Figure 10:
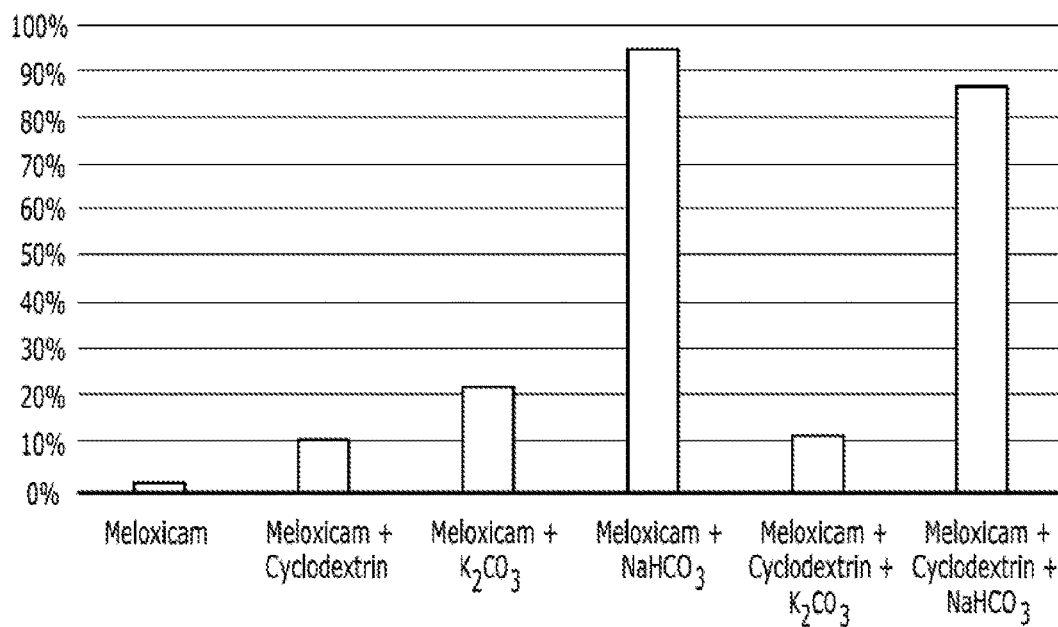
FIG. 10 is another depiction of the results described in Example 2 and contained in Table 6.

Provided herein are dosage forms with NSAIDs (such as meloxicam) and cyclodextrin (optionally in an inclusion complex), and/or bicarbonate, and methods of treatment using the dosage form.

A dosage form may be given enterally including, but not limited to, oral, sublingual, or rectal delivery, or parenterally including, but not limited to, intravenous, intramuscular, intranasal, or subcutaneous delivery.

Some methods include administration of a product that combines an NSAID that is formulated with: a) a cyclodextrin and/or b) a buffering agent. In some embodiments, the method involves treating a patient with a pharmaceutical formulation comprising meloxicam and a cyclodextrin and/or a carbonate/bicarbonate. Method embodiments may also include treating a patient to increase the bioavailability of meloxicam in the patient or increase the rate at which the meloxicam becomes bioavailable.

Unless otherwise indicated, any reference to a compound herein, such as meloxicam or rizatriptan, by structure, name, or any other means, includes pharmaceutically acceptable salts, alternate solid forms, such as polymorphs, solvates, hydrates, enantiomers, tautomers, deuterium-modified forms, or any other chemical species, such as precursors, prodrugs, or any other chemical species that may rapidly convert to a compound described herein under conditions in which the compounds are used as described herein.

A subject combination may be given enterally including, but not limited to, oral, sublingual, or rectal delivery, or parenterally including, but not limited to, intravenous, intramuscular, intranasal, or subcutaneous delivery. In some embodiments, both meloxicam and rizatriptan are administered orally. In some embodiments, meloxicam is administered intravenously and rizatriptan is administered orally. In some embodiments, meloxicam is administered intramuscularly and rizatriptan is administered orally.

Normally, the combination of meloxicam and rizatriptan is administered so that the human being receives the meloxicam and rizatriptan within a short period of time with respect to one another. For example, the meloxicam and rizatriptan may be administered within about 2 hours, within about 1 hour, within about 30 minutes, within about 20 minutes, within about 15 minutes, within about 10 minutes, within about 5 minutes, or within about 1 minute of one another. In some embodiments, the meloxicam and rizatriptan are administered simultaneously, which for the purpose of this disclosure includes administration within about 5 minutes. In some embodiments, the meloxicam and rizatriptan are administered in a single dosage form.

The term "treating" or "treatment" broadly includes any kind of treatment activity, including the diagnosis, cure, mitigation, or prevention of disease in man or other animals, or any activity that otherwise affects the structure or any function of the body of man or other animals.

The dosage form or the subject combination may be used to treat, or provide relief of, any type of pain including, but not limited to, migraine and other types of headache, inflammatory pain, musculoskeletal pain, neuropathic pain, chronic pain, acute pain, localized pain, systemic pain, cancer-related pain, acute pain, pain due to injury, pain due to illness (e.g., fever), post-operative pain, etc. In some instances, pain relief may be palliative, or pain relief may be provided independent of improvement of the disease or condition or the underlying cause of the disease or condition. For example, although the underlying disease may not improve, or may continue to progress, an individual suffering from the disease may experience pain relief. In some embodiments, the pain affects a muscle, nerve, cartilage, bone, ligament, tendon, tendon sheaths, bursae, or joint.

Migraine is a headache disorder characterized by recurrent headaches that may be moderate to severe. The headaches may affect one half of the head, may be pulsating in nature, and may last from 2 to 72 hours. Associated symptoms may include nausea, vomiting, and sensitivity to light (photophobia), sound (phonophobia), or smell. The pain can be made worse by physical activity. Migraines may be associated with an aura, which may be a short period of visual disturbance which signals that the headache will soon occur.

Administering a subject combination to a human being suffering from migraine, such as an acute attack of migraine pain or aura, may quickly result in a reduction in a migraine symptom, such as pain, nausea, vomiting, photophobia, or phonophobia, such as at or within about 5 minutes (intended as a shorthand for "at about 5 minutes, or within about 5 minutes"), at or within about 10 minutes, at or within about 30 minutes, at or within about 1 hour, at or within about 90 minutes, at or within about 2 hours, at or within about 2.5 hours, or at or within about 3 hours. In some embodiments, a human being experiences a reduction of, or complete relief from, pain, such as headache pain or migraine pain, nausea, vomiting, photophobia, and/or phonophobia, at or within about 1 hour, at or within about 90 minutes, at or within about 2 hours, at or within about 2.5 hours, or at or within about 3 hours. In some embodiments, the relief experienced, is greater than would be experienced by receiving the same amount of rizatriptan without meloxicam. In some embodiments, the relief experienced, is greater than would be experienced by receiving the same amount of meloxicam without rizatriptan.

Observation of relief or reduction in a symptom at a specific period of time, such as "at 2 hours," is useful because it allows the effectiveness of the treatment to be evaluated at a specific or consistent time point, which facilitates comparison between patients. Observation of relief or reduction in a symptom within a specific period of time, such as "within about 2 hours," is useful because it is desirable for relief or reduction of a symptom to occur as early as possible, and specifying that relief occur within a specified time sets a guideline in which it is desirable that relief occur.

For some methods, administration of the subject combination may achieve a reduction in migraine pain, nausea, vomiting, photophobia, or phonophobia that lasts at least about one hour, at least about two hours, at least about three hours, at least about four hours, at least about six hours, at least about eight hours, about 8-24 hours, about 24 hours, or more than 24 hours.

In some embodiments, the meloxicam and the rizatriptan are administered simultaneously (e.g. in a single dosage form, such as a single oral dosage form), and two hours after the meloxicam and the rizatriptan are administered, the human being experiences greater pain relief than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater pain relief than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater pain relief than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater pain relief than the human being would have experienced twenty-four hours after receiving the same amount of rizatriptan without the meloxicam.

In some embodiments, the meloxicam and the rizatriptan are administered simultaneously (e.g. in a single dosage form, such as a single oral dosage form), and two hours after the meloxicam and the rizatriptan are administered, the human being experiences greater relief from nausea than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from nausea than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from nausea than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from nausea than the human being would have experienced twenty-four hours after receiving the same amount of rizatriptan without the meloxicam.

In some embodiments, the meloxicam and the rizatriptan are administered simultaneously (e.g. in a single dosage form, such as a single oral dosage form), and two hours after the meloxicam and the rizatriptan are administered, the human being experiences greater relief from vomiting than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from vomiting than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from vomiting than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from vomiting than the human being would have experienced twenty-four hours after receiving the same amount of rizatriptan without the meloxicam. In some embodiments, the meloxicam and the rizatriptan are administered simultaneously (e.g. in a single dosage form, such as a single oral dosage form), and two hours after the meloxicam and the rizatriptan are administered, the human being experiences greater relief from photophobia than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from photophobia than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from photophobia than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from photophobia than the human being would have experienced twenty-four hours after receiving the same amount of rizatriptan without the meloxicam.

In some embodiments, the meloxicam and the rizatriptan are administered simultaneously (e.g. in a single dosage form, such as a single oral dosage form), and two hours after the meloxicam and the rizatriptan are administered, the human being experiences greater relief from phonophobia than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from phonophobia than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from phonophobia than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from phonophobia than the human being would have experienced twenty-four hours after receiving the same amount of rizatriptan without the meloxicam.

In some embodiments, the human being receiving the subject combination has a history of inadequate response to prior migraine treatments. For example, if the human being is asked whether he or she was pain-free within two hours of treatment for most attacks, and given the option of answering "never," "rarely," "less than half the time," or "half the time or more;" and the human being answers "never," "rarely," or "less than half the time," then the human being has had an inadequate response to the treatment. Similarly, if the human being is asked whether one dose of medication usually relieved the human being's headache and kept it away for at least 24 hours, and given the option of answering "never," "rarely," "less than half the time," or "half the time or more;" and the human being answers "never," "rarely," or "less than half the time," then the human being has had an inadequate response to the treatment.

In some embodiments, the human being receiving the subject combination has indicated that he or she was "never" pain-free within two hours of treatment for most attacks. In some embodiments, the human being receiving the subject combination has indicated that he or she was "rarely" pain-free within two hours of treatment for most attacks. In some embodiments, the human being receiving the subject combination has indicated that he or she was pain-free within two hours of treatment for most attacks "less than half the time."

In some embodiments, the human being receiving the subject combination has indicated that one dose of medication "never" relieved the respondent's headache and kept it away for at least 24 hours. In some embodiments, the human being receiving the subject combination has indicated that one dose of medication "rarely" relieved the respondent's headache and kept it away for at least 24 hours. In some embodiments, the human being receiving the subject combination has indicated that one dose of medication relieved the respondent's headache and kept it away for at least 24 hours "less than half the time."

In some embodiments, the dosage form may also be administered to relieve arthritis pain. In some embodiments the dosage form may be administered to relieve other signs and/or symptoms of arthritis. Examples of arthritis include, but are not limited to, rheumatoid arthritis, juvenile rheumatoid arthritis (pauciarticular and polyarticular course), osteoarthritis, erosive osteoarthritis, sero-negative (non-rheumatoid), arthropathies, non-articular rheumatism, peri-articular disorders, axial spondyloarthritis, transient osteoarthritis of the hip, vertebral crush fractures, osteoporosis, and neuropathic arthropathies including Charcot's foot, axial spondyloarthritis including ankylosing spondylitis, and SAPHO syndrome. In other embodiments, the arthritis pain may be chronic or acute. In some embodiments the dosage form may be administered to relief the signs and/or symptoms of an arthritis including but not limited osteoarthritis For some methods, administration of the dosage form may achieve a reduction in pain that lasts at least about one hour, two hours, three hours, four hours, six hours, at least about eight hours, about eight to about 24 hours, or about 24 hours. In other embodiments, administration of the dosage form may achieve a reduction in pain that is observed at about 10 minutes, at about 30 minutes, at about one hour, at about two hours, at about three hours, at about four hours, at about five hours, at about six hours, at less than 15 minutes, at less than 20 minutes, 30 minutes, at less than one hour, at less than two hours, at less than three hours, at about 5, 10, 15, 20, 25, 30, 35, 40, 45, 50, or 60 minutes, or other time period bound by these ranges, after administration of the dosage form.

In some embodiments, the dosage form may also be administered to relieve neuropathic pain, including diabetic peripheral neuropathy, post-herpetic neuralgia, trigeminal neuralgia, monoradiculopathies, phantom limb pain, sciatica, pudendal neuralgia, and central pain. Other causes of neuropathic pain may include, but are not limited to, cancer-related pain, lumbar nerve root compression, spinal cord injury, post-stroke pain, central multiple sclerosis pain, HIV-associated neuropathy, and radio-therapy or chemotherapy associated neuropathy. The neuropathic pain treated may be chronic or acute.

In some methods, the dosage form may be administered to relieve inflammatory pain including inflammatory musculoskeletal pain, pain due to injury, arthritis pain, and complex regional pain syndrome. In other embodiments, the inflammatory pain may be chronic or acute.

Arthritis refers to inflammatory joint diseases that can be associated with pain. Examples of arthritis pain include but are not limited to pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome. The inflammatory joint disease treated may be chronic or acute.

For some methods, the meloxicam may be administered to relieve musculoskeletal pain. Examples of musculoskeletal pain may include, but are not limited to, back pain, low back pain (e.g., lumbosacral pain), neck pain, infection, cramps, tendonitis, epidondylitis, carpal tunnel syndrome, joint pain, fibromyalgia, pain due to injury, Tunnel syndromes, pain associated with bone fractures, sprains, fibrous dysplasia, osteogenesis imperfecta, Paget's disease of bone, transient osteoporosis, and transient osteoporosis of the hip. In other embodiments, the musculoskeletal pain may be chronic or acute.

For some methods, administration of the dosage form or the subject combination may achieve a reduction in pain that lasts at least about one hour, at least about two hours, at least about three hours, at least about four hours, at least about six hours, at least about eight hours, about 8 to about 24 hours, or about 24 hours. In other embodiments, administration of the subject combination may achieve a reduction in pain that is observed at about 10 minutes, at about 30 minutes, at about one hour, at about two hours, at about three hours, at about four hours, at about five hours, at about six hours, at or within about 5 minutes, at or within about 10 minutes, at or within about 15 minutes, at or within about 20 minutes, at or within about 25 minutes, at or within about 30 minutes, at or within about 35 minutes, at or within about 40 minutes, at or within about 45 minutes, at or within about 50 minutes, or at or within about 60 minutes, at two hours or less, at three hours or less, or other time period bound by these ranges, after administration of the subject combination.

A human being that is treated for a disease or condition with the dosage forms described herein may be of any age. For example the person may have an age of about 10 years to about 90 years, about 20 years to about 80 years, about 30 years to about 75 years, about 40 years to about 70 years, about 1 year to about 16 years, about 80 years to about 95 years, about 18 years or more, about 20 years or more, about 25 years or more, about 30 years or more, about 40 years or more, about 45 years or more, about 50 years or more, about 55 years or more, about 60 years or more, about 65 years or more, or any other age in a range bounded by, or between, these values.

In some embodiments, a human being that is treated for a disease or condition with a dosage form comprising meloxicam or another NSAID has suffered from the pain or condition associated with the pain for at least 1 day, at least one week, at least 2 weeks, at least 1 month, at least 6 weeks, at least 2 months, at least 3 months, at least 6 months, or at least 1 year, or any duration in a range bounded by, or between, these values.

A cyclodextrin used in a dosage form with meloxicam could include a cyclodextrin, a cyclodextrin derivative, and/or a salt thereof. An inclusion complex of meloxicam and cyclodextrin may be more water-soluble relative to the non-complexed meloxicam. The cyclodextrin may be a naturally-occurring cyclodextrin (e.g., α, β, or γ-cyclodextrins) or a synthetic cyclodextrin. In some embodiments, α-cyclodextrins, derivatives, or salts thereof may be used. α-Cyclodextrins may include, but are not limited to, (2,3,6-tri-O-acetyl)-α-cyclodextrin, (2,3,6-tri-O-methyl)-α-cyclodextrin, (2,3,6-tri-O-octyl)-α-cyclodextrin, 6-bromo-6-deoxy-α-cyclodextrin, 6-iodo-6-deoxy-α-cyclodextrin, (6-O-tertbutyl-dimethylsilyl)-α-cyclodextrin, butyl-α-cyclodextrin, succinyl-α-cyclodextrin, (2-hydroxypropyl)-α-cyclodextrin, or combinations thereof.

In some embodiments, β-cyclodextrins, derivatives, or salts thereof may be used. β-cyclodextrins may include, but are not limited to, hydroxypropyl-β-cyclodextrin, 6-monodeoxy-6-monoamino-β-cyclodextrin, glucosyl-β-cyclodextrin, maltosyl-β-cyclodextrin, 6-O-α-D-glucosyl-β-cyclodextrin, 6-O-α-maltosyl-β-cyclodextrin, 6-azido-6-deoxy-β-cyclodextrin, (2,3-di-O-acetyl-6-O-sulfo)-β-cyclodextrin, methyl-β-cyclodextrin, dimethyl-β-cyclodextrin (DMβCD), trimethyl-β-cyclodextrin (TMβCD), (2,3-di-O-methyl-6-O-sulfo)-β-cyclodextrin, (2,6-di-O-methyl)-β-cyclodextrin, (2,6-di-O-ethyl)-β-cyclodextrin, (2,3,6-tri-O-methyl)-β-cyclodextrin, (2,3,6-tri-O-acetyl)-β-cyclodextrin, -(2,3,6-tri-O-benzoyl)-β-cyclodextrin, (2,3,6-tri-O-ethyl)-β-cyclodextrin, 6-iodo-6-deoxy-β-cyclodextrin, 6-(dimethyl-tert-butylsilyl)-6-deoxy-β-cyclodextrin, 6-bromo-6-deoxy-β-cyclodextrin, monoacetyl-β-cyclodextrin, diacetyl-β-cyclodextrin, triacetyl-β-cyclodextrin, (3-O-acetyl-2,6-di-O-methyl)-β-cyclodextrin, (6-O-maltosyl)-β-cyclodextrin, (6-O-sulfo)-β-cyclodextrin, (6-O-t-butyldimethylsilyl-2,3-di-O-acetyl)-β-cyclodextrin, succinyl-(2-hydroxypropyl)-β-cyclodextrin, (2,6-di-O-)ethyl-β-cyclodextrin, (2-carboxyethyl)-β-cyclodextrin (CMEβCD), hydroxyethyl-β-cyclodextrin (HEβCD), (2-hydroxypropyl)-β-cyclodextrin, (2-hydroxypropyl)-β-cyclodextrin (HPβCD), (3-hydroxypropyl)-β-cyclodextrin (3HPβCD), (2,3-hydroxypropyl)-β-cyclodextrin (DHPβCD), butyl-β-cyclodextrin, methyl-β-cyclodextrin, silyl((6-O-tert-butyldimethyl)-2,3,-di-O-acetyl)-β-cyclodextrin, succinyl-β-cyclodextrin, (2-hydroxyisobutyl)-β-cyclodextrin, randomly methylated-β-cyclodextrin, branched-β-cyclodextrin, or combinations thereof.

In other embodiments, a β-cyclodextrin may be a sulfoalkyl ether cyclodextrin, derivative, or salt thereof. Examples of sulfoalkyl ether cyclodextrin derivatives may include, but are not limited to, sulfobutyl ether-β-cyclodextrin (e.g., SBEβCD, betadex, CAPTISOL®). In some embodiments, a SBEβCD may have about 4-8, about 5-8, about 4-7, about 6-7, or about 6.5 sulfobutyl ether groups per cyclodextrin molecule.

In some embodiments, γ-cyclodextrins, derivatives, or salts thereof may be used. γ-cyclodextrins may include carboxymethyl-γ-cyclodextrin, (2,3,6-tri-O-acetyl)-γ-cyclodextrin, (2,3,6-tri-O-methyl)-γ-cyclodextrin, (2,6-di-O-pentyl)-γ-cyclodextrin, 6-(dimethyl-tert-butylsilyl)-6-deoxy-γ-cyclodextrin, 6-bromo-6-deoxy-γ-cyclodextrin, 6-iodo-6-deoxy-γ-cyclodextrin, (6-O-t-butyldimethylsilyl)-γ-cyclodextrin, succinyl-γ-cyclodextrin, hydroxypropyl-γ-cyclodextrin (2-hydroxypropyl)-γ-cyclodextrin, acetyl-γ-cyclodextrin, butyl-γ-cyclodextrin, or combinations thereof.

In some embodiments, the dosage form may include a bicarbonate, such as sodium bicarbonate, potassium bicarbonate, magnesium bicarbonate, calcium bicarbonate, ammonium bicarbonate, or a combination thereof. A bicarbonate may help to increase bioavailability of the meloxicam.

In other embodiments, the dosage form may include a carbonate, derivatives, or salts thereof. Examples of carbonates may include aluminum carbonate, ammonium carbonate, barium carbonate, calcium carbonate, cobalt(II) carbonate, lanthanum carbonate, lithium carbonate, magnesium carbonate, manganese(II) carbonate, potassium carbonate, sodium carbonate, or combinations thereof.

In some embodiments, enhanced bioavailability of the dosage form may be achieved in treating one of these conditions by administering a dosage form comprising a salt form of the meloxicam, by creating an inclusion complex with meloxicam and cyclodextrin, and/or by including a bicarbonate. This may allow a reduced molar amount of the meloxicam to be used as compared to other meloxicam dosage forms.

Unless otherwise indicated, any reference to a compound herein, such as meloxicam or a cyclodextrin, by structure, name, or any other means, includes pharmaceutically acceptable salts, alternate solid forms, such as polymorphs, solvates, hydrates, enantiomers, tautomers, deuterium-modified forms, or any other chemical species that may rapidly convert to a compound described herein under conditions in which the compounds are used as described herein.

In some embodiments, use of a cyclodextrin, a carbonate, or a bicarbonate may improve the oral bioavailability of meloxicam by at least about 10%, at least about 20%, at least about 30%, at least about 40%, at least about 50%, at least about 60%, at least about 70%, at least about 80%, at least about 90%, up to about 100%, up to about 200%, or any amount in a range bounded by, or between, these values as compared to administration of meloxicam alone.

Due to the improved bioavailability, the dosage form may contain, or a subject may receive, on a molar basis, less of the meloxicam than would otherwise be administered. For example, a dosage form may contain, or a mammal may receive, at least about 10 mole % less, at least about 20 mole % less, at least about 30 mole % less, at least about 40 mole % less, at least about 50 mole % less, at least about 60 mole % less, at least about 70 mole % less, at least about 80 mole % less, at least about 85 mole % less, and/or up to about 90 mole % less, 95 mole % less, or any amount in a range bounded by, or between, these values as would otherwise be administered of meloxicam.

In other embodiments, use of other NSAIDs, opioids, or other pain medications may be reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, up to about 100%, as compared to the use of other NSAIDs, opioids or other pain medications without administration of meloxicam with cyclodextrin, carbonate, and/or bicarbonate.

In some embodiments, a dosage form may contain meloxicam in an amount from about 1-50 mg; about 1-10 mg; about 1-5 mg; about 10-40 mg; about 1-35 mg; about 1-25 mg; about 1-15 mg; about 5-20 mg; about 5-10 mg; about 5-15 mg; about 10-20 mg; about 20-30 mg; about 30-40 mg; about 40-50 mg; about 5 mg; about 7.5 mg; about 10 mg; about 15 mg; about 30 mg; or any amount in a range bounded by, or between, any of these values. These doses may be a safe dose for repeated administration, such as once hourly dosing to once daily dosing, twice daily dosing, dosing one to 12 times daily, doing 3, 4, 5, or 6 times daily, etc. In some embodiments, the meloxicam may be safely administered 2, 3, 4, 5, 6, 7, 8, 9, 10, 11, 12, 13, 14, or 15 times, or about 3 to about 10 times a day, once a day, or less frequently, such as once a week, once every two weeks, once a month, etc.

For some dosage forms, meloxicam forms a complex with the substituted-β-cyclodextrin or other another cyclodextrin which may be formulated into a solid dosage form. Such a dosage form may be suitable for oral administration. A meloxicam-cyclodextrin inclusion complex may also be dissolved in water or another solvent to form a parenteral formulation. However, physical mixtures of meloxicam and the substituted-β-cyclodextrin or other cyclodextrins may also be used in oral or parenteral dosage forms.

Formation of an inclusion complex of meloxicam and a cyclodextrin may help to improve the properties of a dosage form. For some inclusion complexes, the meloxicam and the cyclodextrin (e.g., SBEβCD) may have a molar ratio of about 0.5-2 (a molar ratio of 0.5 is 0.5 moles of meloxicam to 1 mole of cyclodextrin), about 0.5-0.7, about 0.6-0.8, about 0.7-0.9, about 0.8-1, about 0.9-1.1, about 1-1.2, about 1.1-1.3, about 1.2-1.4, about 1.3-1.5, about 1.4-1.6, about 1.5-1.7, about 1.6-1.8, about 1.7-1.9, about 1.8-2, about 0.8-1.2, about 1, or any ratio in a range bounded by any of these values.

For some dosage forms, a cyclodextrin (e.g., SBEβCD) may be employed in a weight ratio to the meloxicam within the range from about 1-1000 (e.g. 1 g of cyclodextrin per 1 g of meloxicam is a weight ratio of 1); about 1-20; about 1-10; about 1-15; about 2-4, about 3-5, about 4-6, about 5-7, about 6-8, about 7-9, about 8-10, or any weight ratio in a range bounded by, or between, any of these values. For some dosage forms, a cyclodextrin (e.g., SBEβCD) may be employed in a weight ratio to the meloxicam within the range from about 0.001-1 (e.g. 0.1 g of cyclodextrin per 1 g of meloxicam is a weight ratio of 0.1); about 0.01-1; about 0.05-1; about 0.1-1; about 0.2-1; about 0.3-1, about 0.4-1, about 0.5-1, about 0.6-1, about 0.7-1, about 0.8-1, or any weight ratio in a range bounded by, or between, any of these values. Each type of cyclodextrin employed may have a different ratio.

For some dosage forms, the cyclodextrin may be present in an amount from about 1-200 mg; 25-175 mg; about 50-150 mg; about 25-100 mg; about 75-150 mg; about 100-175 mg; about 20-80 mg; about 25-50 mg; about 60-100 mg; about 80-100 mg; about 80-120 mg; about 100-120 mg; about 100-140 mg; about 120-160 mg; about 140-180 mg; about 30-90 mg; about 40-80 mg; about 50-70 mg, about 55-65 mg, about 60-62 mg, or any amount in a range bounded by, or between, any of these values.

For some methods, the inclusion complex of meloxicam and cyclodextrin such as a substituted-β-cyclodextrin is delivered orally (for example by tablet, capsule, elixir, or the like). Other potential routes of administration include intravenous, intramuscular, intranasal, lyophilized parenteral, subcutaneous, transdermal, transmucosal, or through other parenteral means. The meloxicam may also be delivered alone or non-complexed with cyclodextrin.

Some dosage forms contain a bicarbonate (e.g., sodium bicarbonate) in amount from about 1-2000 mg; about 1-1000 mg; about 100-1000 mg; about 200-800 mg; about 1-500 mg; about 1-200 mg; about 1-100 mg; about 50-750 mg; about 500-1000 mg; about 100-500 mg; about 100-300 mg; about 500-1000 mg; about 300-700 mg; about 400-600 mg; about 50-250 mg; about 250-750 mg; about 100-200 mg; about 200-300 mg; about 300-400 mg; about 400-500 mg; about 410-510 mg; about 420-520 mg; about 430-530 mg; about 440-540 mg; about 450-550 mg; about 460-560 mg; about 470-570 mg; about 480-580 mg; about 490-590 mg; about 500-600 mg; about 600-700 mg; about 700-800 mg; about 800-900 mg; about 150-650 mg; about 350-850 mg; or any amount in a range bounded by, or between, any of these values.

Some dosage forms contain a carbonate in amount from about 1-1000 mg; about 1-500 mg; about 1-200 mg; about 1-100 mg; about 50-750 mg; about 500-1000 mg; about 100-500 mg; about 100-300 mg; about 200-800 mg; about 500-1000 mg; about 300-700 mg; about 400-600 mg; about 50-250 mg; about 250-750 mg; about 100-200 mg; about 200-300 mg; about 300-400 mg; about 400-500 mg; about 500-600 mg; about 600-700 mg; about 700-800 mg; about 800-900 mg; about 150-650 mg; about 350-850 mg; or any amount in a range bounded by, or between, any of these values.

In some embodiments, the daily dose of meloxicam (e.g., an oral dose, a parenteral dose, etc.) is about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 5-10 mg, about 10-15 mg, about 15-20 mg, about 20-25 mg, about 25-30 mg, about 30-35 mg, or any amount in a range bounded by any of these values.

In some embodiments, the weekly dose of meloxicam (e.g., an oral dose) is about 1-1000 mg; about 1-500 mg; about 10-250 mg; about 100-300 mg; about 10-100 mg; about 10-150 mg; about 10-300 mg; about 20-150 mg; about 20-60 mg; about 30-70 mg; about 40-60 mg; about 50-70 mg; about 70-90 mg; about 90-110 mg; about 50 mg; about 55 mg; about 100-150 mg; about 30-100 mg; or any amount in a range bounded by, or between, any of these values. The weekly dose may be given as a single dose, given once during the week, or may be given in 2, 3, 4, 5, 6, or 7 individual doses during the week.

In some embodiments, the monthly dose of meloxicam (e.g., an oral dose), or a dose administered over a period of a month, is about 5000 mg or less; about 4000 mg or less; about 3000 mg or less; about 2000 mg or less; about 1000 mg or less; about 700 mg or less; about 600 mg or less; about 1-4000 mg; about 1-1000 mg; about 10-1000 mg; about 50-1000 mg; about 10-600 mg; about 40-600 mg; about 50-600 mg; about 40-400 mg; about 50-200 mg; about 200-240 mg; about 240-280 mg; about 280-320 mg; about 320-360 mg; about 360-400 mg; about 400-450 mg; about 450-500 mg; about 500-600 mg; about 250-350 mg; about 100-600 mg; about 40-2000 mg; about 40-800 mg; about 100-900 mg; about 100-800 mg; about 40-1000 mg; about 50-1000 mg; about 100-1000 mg; or any monthly dose in a range bounded by, or between, any of these values. A monthly dose may be given as a single dose, or as two or more individual doses administered during the month. In some embodiments, the monthly dose is administered in 2 or 3 bi-weekly doses. In some embodiments, the monthly dose is administered in 4 or 5 weekly doses. In some embodiments, the monthly dose is administered in 28 to 31 daily doses, or in 56 to 62 daily doses or more. In some embodiments, the monthly dose is administered in 5 to 15 individual doses during the month. The monthly dose may be administered for only 1 month, or may be repeatedly administered for 2 or more months.

In other embodiments, the dosage form may be administered weekly for about one, two, three, four, or more consecutive weeks, every other week or bi-weekly, or once every three weeks. This regimen may be repeated once weekly, twice in a month, three times in a month, once monthly, once every two months, once every three months, or as directed by a medical professional.

In certain embodiments, the pharmaceutical composition results in increased bioavailability (e.g., reduced $T_{max}$, increased $C_{max}$, increased AUC, etc.) of the meloxicam from the dosage form as compared to a dosage form containing meloxicam but not containing a cyclodextrin, an acid inhibitor, or a buffering agent (such as a bicarbonate). In some embodiments, the bioavailability of meloxicam will increase with multiple dosing. For example, the bioavailability of meloxicam in the dosage form may increase after about 1-10 days of dosing; about 2-6 days of dosing; about 3-5 days of dosing; about 4-6 days of dosing; about 5-8 days of dosing; about 5 days of dosing; about 6 days of dosing; about 7 days of dosing; about 8 days of dosing; about 10 days of dosing; about 15 days of dosing; or time in any range bounded by, or between, any of these values; as compared to the bioavailability of meloxicam in a dosage form not containing a cyclodextrin, an acid inhibitor, or a buffering agent (such as a bicarbonate).

Some of the dosage forms may result in a desired range for an area under the plasma concentration curve (AUC) of meloxicam. For example the dosage with meloxicam may result in an AUC of meloxicam of about 1-150 µg·hr/mL; about 10-30 µg·hr/mL; about 20-40 µg·hr/mL; about 30-50 µg·hr/mL; about 40-60 µg·hr/mL; about 50-70 µg·hr/mL; about 60-80 µg·hr/mL; about 70-90 µg·hr/mL; about 80-100 µg·hr/mL; about 10-100 µg·hr/mL; about 50-150 µg·hr/mL; about 25-125 µg·hr/mL; about 75-150 µg·hr/mL; about 20-50 µg·hr/mL; about 40-70 µg·hr/mL; about 60-90 µg·hr/mL; about 80-110 µg·hr/mL; about 100-130 µg·hr/mL; about 120-150 µg·hr/mL; or any AUC in a range bounded by, or between, any of these values.

Unless otherwise indicated, the AUC refers to the AUC calculated to the last measured concentration ($AUC_{0-t}$), such as, over a period of 6 hours ($AUC_{0-6}$), over a period of 12 hours ($AUC_{0-12}$), over a period of 24 hours ($AUC_{0-24}$), or extrapolated to infinity ($AUC_{0-inf}$).

In Example 3 below, the $AUC_{0-24}$ of meloxicam in human beings for an oral dosage form containing sodium bicarbonate and sulfobutylether β-cyclodextrin (SBEβCD) was about 27 µg·hr/mL. This dosage form contained 15 mg of meloxicam.

The 15 mg IV and intramuscular doses also provide an $AUC_{0-24}$ of meloxicam in human beings that is about 27 µg·hr/mL. The AUC of meloxicam is believed to be approximately dose proportional. So for this oral dosage form, or for an IV or intramuscular dosage form, a meloxicam dose of, for example, approximately 17 mg to about 30 mg would be expected to result in an $AUC_{0-24}$ of meloxicam of about 30-50 µg·hr/mL.

For some acute pain conditions, such as migraine and other types of headache, the AUC for a short period after oral administration, such as an AUC measured over 6 hours (or $AUC_{0-6}$), may be of particular interest. For example, some dosage forms may result in an $AUC_{0-6}$ of at least about 6 µg·hr/mL; at least about 7 µg·hr/mL; at least about 8 µg·hr/mL; at least about 9 µg·hr/mL; about 6-10 µg·hr/mL; about 7-11 µg·hr/mL; about 8-12 µg·hr/mL; about 9-13 µg·hr/mL; or any AUC in a range bounded by, or between, any of these values.

In some embodiments, the dosage form may result in a $C_{max}$ of meloxicam of about 10-2500 ng/mL; about 100-2250 ng/mL; about 500-2000 ng/mL; about 1000-2500 ng/mL; about 1000-2000 ng/mL; about 100-900 ng/mL; about 750-1500 ng/mL; about 1250-2000 ng/mL; about 1500-2300 ng/mL; about 800-1200 ng/mL; about 1900-2400 ng/mL; about 50-500 ng/mL; about 400-950 ng/mL; about 900-1500 ng/mL; about 1100-2200 ng/mL; about 1300-1600 ng/mL; about 1200-1500 ng/mL; about 1400-2100 ng/mL; about 1500-1900 ng/mL; about 1600-2100 ng/mL; about 1700-2000 ng/mL; about 1800-2000 ng/mL; about 1900-2500 ng/mL; about 150-1700 ng/mL; about 1600-1800 ng/mL; about 1700-1900 ng/mL; about 1800-2000 ng/mL; about 1900-2100 ng/mL; about 2000-2200 ng/mL; about 2100-2300 ng/mL; about 2200-2400 ng/mL; about 2300-2500 ng/mL; about 2500-3000 ng/mL; or any $C_{max}$ in a range bounded by, or between, any of these values.

For example, a method described herein may reduce the $T_{max}$ of meloxicam. In some embodiments, the method may include treating a patient to achieve the $T_{max}$ of meloxicam in the patient within about 10 minutes; about 20 minutes; about 30 minutes; about 40 minutes; about 50 minutes; about 60 minutes; about 70 minutes; about 80 minutes; about 90 minutes; about 100 minutes; about 110 minutes; about 120 minutes; about 180 minutes; about 1-10 hr; about 2-9 hr; about 3-7 hr; about 4-6 hr; about 1-5 hr; about 2-7 hr; about 3-8 hr; about 4-9 hr; about 1-4 hr; about 2-5 hr; about 3-6 hr; about 4-7 hr; about 5-8 hr; about 6-9 hr; about 7-10 hr; after administration or any $T_{max}$ in a range bounded by, or between, any of these values.

In some embodiments, an oral dosage form may have a $T_{max}$ of meloxicam that is shorter than would be achieved by administering meloxicam by intramuscular injection. In some embodiments, an oral dosage form may have a $T_{max}$ of meloxicam that is shorter, or may increase meloxicam plasma levels at a faster rate, by a factor of at least about 1.5, about 2, about 3, about 4, about 5, about 6, about 7, about 8, about 9, about 10, about 12, about 15, about 20, or by a factor of about 1.5-1000, about 2-100, about 3-100, about 4-100, about 5-100, about 6-100, about 7-100, about 8-100, about 9-100, about 10-100, about 12-100, about 15-100, about 20-100, or by a factor in a range bounded by any of these values.

In some embodiments, a dosage form comprising meloxicam may result in a plasma concentration of meloxicam at 12 hours that is about 0.01-0.5 µg/mL; about 0.5-0.7 µg/mL; about 0.6-0.8 µg/mL; about 0.7-0.9 µg/mL; about 0.8-1 µg/mL; about 0.9-1.1 µg/mL; about 1-1.2 µg/mL; about 1.1-1.3 µg/mL; about 1.2-1.4 µg/mL; about 1.3-1.5 µg/mL; about 1.4-1.6 µg/mL; about 1.5-1.7 µg/mL; about 1.6-1.8 µg/mL; about 1.7-1.9 µg/mL; about 1.8-2 µg/mL; about 1.9-2.1 µg/mL; about 2-2.2 µg/mL; about 2.1-2.3 µg/mL; about 2.2-2.4 µg/mL; about 2.3-2.5 µg/mL; about 2.4-2.6 µg/mL; about 2.5-2.7 µg/mL; about 2.6-2.8 µg/mL; about 2.7-2.9 µg/mL; about 2.8-3 µg/mL; about 2.9-3.1 µg/mL; about 3-3.2 µg/mL; about 3.1-3.3 µg/mL; about 3.2-3.4 µg/mL; about 3.3-3.5 µg/mL; about 3.4-3.6 µg/mL; about 3.5-3.7 µg/mL; about 3.6-3.8 µg/mL; about 3.7-3.9 µg/mL; about 3.8-4 µg/mL; or any plasma concentration in a range bounded by, or between, any of these values.

In some embodiments, meloxicam is administered at a dose that results in a meloxicam plasma level (such as a $C_{ave}$, or average plasma level) of about 0.01-0.5 µg/mL; about 0.5-0.7 µg/mL; about 0.6-0.8 µg/mL; about 0.7-0.9 µg/mL; about 0.8-1 µg/mL; about 0.9-1.1 µg/mL; about 1-1.2 µg/mL; about 1.1-1.3 µg/mL; about 1.2-1.4 µg/mL; about 1.3-1.5 µg/mL; about 1.4-1.6 µg/mL; about 1.5-1.7 µg/mL; about 1.6-1.8 µg/mL; about 1.7-1.9 µg/mL; about 1.8-2 µg/mL; about 1.9-2.1 µg/mL; about 2-2.2 µg/mL; about 2.1-2.3 µg/mL; about 2.2-2.4 µg/mL; about 2.3-2.5 µg/mL; about 2.4-2.6 µg/mL; about 2.5-2.7 µg/mL; about 2.6-2.8 µg/mL; about 2.7-2.9 µg/mL; about 2.8-3 µg/mL; about 2.9-3.1 µg/mL; about 3-3.2 µg/mL; about 3.1-3.3 µg/mL; about 3.2-3.4 µg/mL; about 3.3-3.5 µg/mL; about 3.4-3.6 µg/mL; about 3.5-3.7 µg/mL; about 3.6-3.8 µg/mL; about 3.7-3.9 µg/mL; about 3.8-4 µg/mL; about 0.1-20 µg/mL; about 0.5-15 µg/mL; about 0.5-10 µg/mL; about 5-15 µg/mL; about 10-20 µg/mL; about 7.5-15 µg/mL; about 2-10 µg/mL; about 1-8 µg/mL; about 1-6 µg/mL; about 1-2 µg/mL; about 0.5-3.5 µg/mL; about 0.5-7 µg/mL; about 12-20 µg/mL; about 8-12 µg/mL; about 1-4 µg/mL; about 4-7 µg/mL; about 7-11 µg/mL; about 11-15 µg/mL; about 15-19 µg/mL; about 16-20 µg/mL; or any amount of meloxicam plasma level in a range bounded by, or between, any of these values.

One embodiment is a method for reducing the risk of gastrointestinal side effects in people taking NSAIDs for pain relief and for other conditions, particularly during chronic treatment, and improving the bioavailability of the NSAID. In one embodiment, the method involves the administration of a product that combines: a) an agent that actively raises intragastric pH; and b) an NSAID that is formulated with a cyclodextrin. In another embodiment, the method involves the administration of a product that combines: a) an agent that actively raises intragastric pH; b) an NSAID that is formulated with a cyclodextrin; and c) a buffering agent. Either short or long acting acid inhibitors can be effectively used in the dosage forms. This method has the added benefit of being able to protect patients from other gastrointestinal ulcerogens whose effect may otherwise be enhanced by the disruption of gastroprotective prostaglandins due to NSAID therapy.

The meloxicam formulation in an aqueous parenteral form may include a buffer to adjust the pH of an aqueous formulation, within a range of about 2 to about 5; about 3.5 to about 5; about 5 to about 11; about 6 to about 9; about 6 to about 8; about 6 to about 7; or any other pH in a range bounded by, or between, any of these values. The meloxicam formulation in an oral form may include a buffer to adjust the pH of stomach fluid within a range of about 2 to about 5; about 3.5 to about 5; about 5 to about 11; about 6 to about 9; about 6 to about 8; about 6 to about 7; or any other pH in a range bounded by, or between, any of these values. Examples of buffers suitable for use herein include sulfate buffers, phosphate buffers, borate buffers, carbonate buffers, citrate buffers, etc.

In some embodiments, the dosage form may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, coated tablets, troches, capsules, elixirs, dispersions, suspensions, solutions, syrups, wafers, patches, and the like.

Tablets, troches, pills, capsules and the like may also contain one or more of the following: a binder such as gum tragacanth, acacia, corn starch or gelatin; an excipient, such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the unit dosage form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non-toxic in the amounts employed.

Some compositions or dosage forms may be a liquid, or may comprise a solid phase dispersed in a liquid.

The dosage form may further comprise a second therapeutically active agent, such as an acid inhibitor or an analgesic.

In some embodiments, the dosage form may further comprise an acid inhibitor present in an amount effective to raise the gastric pH of a patient to at least 2, to at least 2.5, to at least 3, to at least 3.5, to at least 4, and more to at least 5, when one or more unit dosage forms are administered. The term "acid inhibitor" refers to agents that inhibit gastric acid secretion and increase gastric pH. Specific $H_2$ blockers, also referred to as $H_2$ antagonists or histamine $H_2$ blockers or antagonists, that may be used include but are not limited to cimetidine, ranitidine, ebrotidine, pabutidine, lafutidine, loxtidine, famotidine, or combinations thereof.

Other agents that may be effectively used as acid inhibitors are the proton pump inhibitors such as omeprazole, esomeprazole, pantoprazole, lansoprazole, dexlansoprazole, rabeprazole, pariprazole, leminoprazole and tenatoprazole. In some embodiments the daily dose of the acid inhibitor is about 1-200 mg, about 1-100 mg, about 1-50 mg, about 40-80 mg, about 5-50 mg, about 20-40 mg, about 10-50 mg, about 10-20 mg, about 20-40 mg, about 15-50 mg, about 30-60 mg, about 10 mg, about 20 mg, about 30 mg, about 40 mg or any other amount in a range bounded by, or between, any of these values.

Examples of particular proton pump inhibitors include esomeprazole, present in unit dosage forms in an amount of between 5 mg and 50 mg; omeprazole, present in unit dosage forms in an amount of between 5 mg and 50 mg; lansoprazole, present in unit dosage forms in an amount of between 5 mg and 150 mg (and preferably at between 5 mg and 30 mg); and pantoprazole, present in unit dosage forms in an amount of between 10 mg and 200 mg. In some embodiments, the proton pump inhibitor is present in the dosage form in an amount of about 10-30 mg, about 20-40 mg, about 30-50 mg, about 40-60 mg, about 50-70 mg, about 60-80 mg, about 70-90 mg, or about 80-100 mg. Recently, a newer class of acid inhibitor has been developed which competes with potassium at the acid pump. The compounds in this class have been referred to as "reversible proton pump inhibitors" or "acid pump antagonists" and may also be used. Examples include AZD-0865, AR-H047108, CS-526, pumaprazole, revaprazan and soraprazan (see WO9605177 and WO9605199). Other compounds in this group are H-335/25 (AstraZeneca, Dialog file 128, accession number 020806); Sch-28080 (Schering Plough, Dialog file 128, accession number 009663); Sch-32651 (Schering Plough, Dialog file 128, accession number 006883) and SK&F-96067 (CAS Registry no. 115607-61-9).

The second therapeutically active agent may include an analgesic such as a second non-steroidal anti-inflammatory drug, an opioid, a steroid, a triptan, etc. In some embodiments, the dosage form or treatment also further comprises administering a second non-steroidal anti-inflammatory drug in an amount effective to reduce or eliminate pain or inflammation. The NSAID may include, but is not limited to, celecoxib, rofecoxib, lumiracoxib, valdecoxib, parecoxib, etoricoxib, CS-502, JTE-522, L-745,337, NS398, aspirin, acetaminophen (considered to be an NSAID for the purposes of the present disclosure), ibuprofen, flurbiprofen, ketoprofen, naproxen, oxaprozin, etodolac, indomethacin, ketorolac, lornoxicam, meloxicam, piroxicam, droxicam, tenoxicam, nabumetone, diclofenac, meclofenamate, mefenamic acid, diflunisal, sulindac, tolmetin, fenoprofen, suprofen, benoxaprofen, aceclofenac, tolfenamic acid, oxyphenbutazone, azapropazone, phenylbutazone, or combinations thereof. It will be understood that, for the purposes of the present disclosure, reference to an acid inhibitor, NSAID, or analgesic agent will include all of the common forms of these compounds and, in particular, their pharmaceutically acceptable salts. The amounts of NSAIDs which are therapeutically effective may be lower in the current embodiments than otherwise found in practice due to potential positive kinetic interaction and NSAID absorption in the presence of an acid inhibitor, and or in the presence of a buffering agent.

In other embodiments, the dosage form or treatment may further comprise administering an opioid in an amount effective to reduce or eliminate pain or inflammation. The opioid may include, but is not limited to, (dextro)propoxyphene, A-methylfentanyl, alfentanil, allylprodine, beziramide, buprenorphine, butorphanol, carfentanyl, desmethylprodine, dextromoramide, dezocine, diacetylmorphine, dihydrocodeinone, dihydroetorphine, dimorphone, diphenoxylate, dipipanone, etorphine, fentanyl, ketobemidone, lefetamine, levacetylmethadol, levomethorphan, levorphanol, loperamide, meperidine, meptazinol, methadone, methylmorphine, morphine, nalbuphine, nalmefene, naloxone, naltrexone, nicomorphine, ohmefentanyl, oripavine, oxycodone, oxymorphone, PEPAP, paramorphine, pentazocine, phenazocine, piritramide, prodine, remifentanil, sufentanil, tapentadol, tilidine, tramadol, or combinations thereof.

Useful triptans may include sumatriptan, rizatriptan, naratriptan, eletriptan, donitriptan, almotriptan, frovatriptan, alvitriptan, zolmatriptan, etc. In some embodiments, the triptan comprises rizatriptan. In some embodiments, the dosage form may contain about 1-5 mg, about 2-6 mg, about 3-7 mg, about 4-8 mg, about 5-10 mg, about 6-11 mg, about 7-12 mg, about 8-13 mg, about 9-14 mg, about 10-15 mg, about 15-20 mg, or about 20-30 mg, of the triptan, such as rizatriptan, or any amount in a range bounded by any of these values.

In some embodiments; a dosage form comprising the subject combination may contain rizatriptan in an amount of about 1-50 mg; about 1-10 mg; about 10-20 mg; about 20-30 mg; about 30-40 mg; or about 40-50 mg; about 10-40 mg; about 1-35 mg; about 1-25 mg; about 1-15 mg; about 1-10 mg; about 5-20 mg; about 1-5 mg; about 2-6 mg; about 3-7 mg; about 4-8 mg; about 5-10 mg; about 6-11 mg; about 7-12 mg; about 8-13 mg; about 9-11 mg; about 9-14 mg; about 10-15 mg; about 11-16 mg; about 12-17 mg; about 13-18 mg; about 14-19 mg; about 15-20 mg; about 5-15 mg; about 0.5 mg; about 1 mg; about 1.5 mg; about 2 mg; about 2.5 mg; about 3 mg; about 3.5 mg; about 4 mg; about 4.5 mg; about 5 mg; about 6 mg; about 7 mg; about 7.5 mg; about 8 mg, about 9 mg, about 10 mg; about 15 mg; about 20 mg, about 25 mg, about 30 mg; or any amount in a range bounded by, or between, any of these values.

For acute migraines, the amount of meloxicam and/or rizatriptan in a single dose, or the AUC of the meloxicam and/or rizatriptan associated with a single dose, is of particular interest. For example, after a single dose, the symptoms may be relieved for an extended period of time, such that, in the short term, repeated doses may not be needed. For more continuous conditions, including more chronic, continuous, or frequent migraine symptoms, daily, weekly, or monthly doses may be of particular interest.

For any amounts of rizatriptan described herein, salt forms of rizatriptan may be present in the amounts recited above, or amounts that are molar equivalents to these amounts for the rizatriptan free base. For example, assuming that the molecular weight of rizatriptan free base is 269.3 g/mol, 10 mg of rizatriptan is 37.1 mmol of rizatriptan. Thus, a molar equivalent of 10 mg of rizatriptan free base would be the mass of 37.1 mmol of that salt form. For example, for the benzoate salt (mw=391.2 g/mol), the molar equivalent of 10 mg of the free base (or 37.1 mmol), would be 14.5 mg. These doses may be safe for repeated administration, such as 1, 2, 3, or 4 times a day, or repeated at an interval of 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 4 weeks, 4-6 weeks, about 1-2 months, about 6 weeks, about 2-3 months, about 3-4 months, about 4-5 months, about 5-6 months, about 6-7 months, about 7-8 months, about 8-9 months, about 9-10 months, about 10-11 months, about 11-12 months, etc.

A pharmaceutical composition may be in the form of a tablet or capsule that has: (a) the acid inhibitor; and/or (b) a buffering agent; and (c) the non-steroidal anti-inflammatory drug (NSAID) present in an amount effective to reduce or eliminate pain or inflammation in a patient upon administration of one or more of said unit dosage forms. The components of the pharmaceutical composition may be in an immediate or extended release form individually or in total.

The term "unit dosage form" as used herein refers to a single entity for drug administration. For example, a single tablet or capsule combining both an acid inhibitor and an NSAID would be a unit dosage form. A "unit dosage form" (or "unit dose form") may also be referred to as a "fixed dosage form" (or "fixed dose form") or "fixed dosage combination" (or "fixed dose combination") and are otherwise interchangeable. In one embodiment, the unit dosage form is a multilayer tablet.

In another embodiment, the unit dosage form is suitable for oral administration to a patient. In yet another embodiment, the unit dosage form is a tablet. In still another embodiment, the unit dosage form is a multilayer tablet comprising a single core and one or more layers outside of the core.

Some dosage forms may comprise a first layer comprising meloxicam, an SBEβCD, and a bicarbonate; and a second layer comprising a second therapeutically active agent and a bicarbonate.

The first layer may contain, for example, any amount of meloxicam in one of the ranges recited above. For example, all of the meloxicam in the dosage form may be present in the first layer. The second layer may contain all of the second therapeutically active agent, such that any amount in the ranges recited above with respect to the second therapeutically active agent may apply to the second layer.

In some embodiments, the first layer contains about 10-200 mg, about 50-150 mg, about 50-100 mg, about 70-120 mg, about 90-140 mg, or about 100 mg of the bicarbonate, such as sodium bicarbonate, or any amount of the bicarbonate in a range bounded by any of these values.

In some embodiments, the second layer contains about 100-500 mg, about 200-500 mg, about 300-500 mg, about 350-450 mg, about 380-420 mg, or about 400 mg of the bicarbonate, such as sodium bicarbonate, or any amount of the bicarbonate in a range bounded by any of these values.

In some embodiments, the pharmaceutical composition may have an effective amount of meloxicam, a cyclodextrin, and a carbonate or bicarbonate to increase bioavailability of meloxicam. In other embodiments, the pharmaceutical composition may have an effective amount of meloxicam, sulfobutylether-β-cyclodextrin (SBEβCD), and sodium bicarbonate to increase bioavailability of meloxicam or reduce the $T_{max}$ of meloxicam.

Some oral dosage forms may have enteric coatings or film coatings. In some embodiments, a dosage form may comprise a tablet or a capsule having an enteric coating. In some embodiments, a dosage form may comprise a tablet or a capsule having a film coating.

An embodiment of the present disclosure is directed to a pharmaceutical composition in unit dosage form suitable for administration to a patient, comprising:
(a) esomeprazole, which may or may not be surrounded by an enteric coating;
(b) sodium or potassium bicarbonate and/or sodium or potassium carbonate; and
(c) meloxicam, which may or may not be formulated with a cyclodextrin, and which may or may not be surrounded by an enteric coating In certain embodiments, the pharmaceutical composition results in faster release or dissolution of the meloxicam from the dosage form as compared to a dosage form containing meloxicam but not containing the acid inhibitor, or not containing the buffering agent.

The following embodiments are contemplated:

Embodiment 1

An inclusion complex of meloxicam in a cyclodextrin.

Embodiment 2

A dosage form comprising: 1) the inclusion complex of embodiment 1, or 2) meloxicam and a carbonate or a bicarbonate.

Embodiment 3

The dosage form of embodiment 2 comprising the inclusion complex, wherein the cyclodextrin comprises substituted β-cyclodextrin.

Embodiment 4

The dosage form of embodiment 3, wherein the substituted β-cyclodextrin is a sulfobutyl ether β-cyclodextrin (SBEβCD) or hydroxypropyl β-cyclodextrin (HPBCD).

Embodiment 5

The dosage form of embodiment 4, wherein the cyclodextrin is the SBEβCD.

Embodiment 6

The dosage form of embodiment 5, wherein the SBEβCD has about 6 to about 7 sulfobutyl ether groups for each molecule of β-cyclodextrin.

Embodiment 7

The dosage form of embodiment 6, wherein the meloxicam and the SBEβCD have a molar ratio of about 0.8 to about 1.2.

Embodiment 8

The dosage form of embodiment 6, wherein the meloxicam and the SBEβCD have a molar ratio of about 1.

Embodiment 9

The dosage form of embodiment 2, 3, 4, 5, 6, 7, or 8, comprising a bicarbonate.

Embodiment 10

The dosage form of embodiment 9, wherein the bicarbonate comprises sodium bicarbonate.

Embodiment 11

The dosage form of embodiment 2, 3, 4, 5, 6, 7, 8, 9, or 10, which is an oral dosage form.

Embodiment 12

The dosage form of embodiment 2, 3, 4, 5, 6, 9, 10, or 11, wherein about 50 mg to about 200 mg of SBEβCD is present in the dosage form.

Embodiment 13

The dosage form of embodiment 2, 3, 4, 5, 6, 7, 8, 9, 10, 11, or 12, wherein the carbonate or bicarbonate is present in an amount in a range of about 400 mg to about 600 mg.

Embodiment 14

The dosage form of embodiment 2, 3, 4, 5, 6, 7, 8, 9, 10, 11, 12, or 13, wherein the $T_{max}$ of meloxicam is decreased as compared to a dosage form not having a carbonate, a bicarbonate, or a cyclodextrin.

Embodiment 15

The method of embodiment 14, wherein the $T_{max}$ of meloxicam is achieved in the patient at a time in a range of about 10 minutes to about 180 minutes after administration.

Embodiment 16

The dosage form of embodiment 2, 3, 4, 5, 6, 7, 8, 9, 10, 11, 12, 13, 14, or 15, having an oral bioavailability of meloxicam that is higher than a dosage form not having a carbonate, a bicarbonate, or a cyclodextrin.

Embodiment 17

The dosage form of embodiment 2, 3, 4, 5, 6, 7, 8, 9, 10, 11, 12, 13, 14, 15, 16, 17, 18, 19, or 20, further comprising an acid inhibitor.

Embodiment 18

The dosage form of embodiment 17, wherein the acid inhibitor is a proton pump inhibitor.

Embodiment 19

The dosage form of embodiment 18, wherein the proton pump inhibitor is esomeprazole.

Embodiment 20

The dosage form of embodiment 19, wherein about 30 mg to about 50 mg of esomeprazole is present in the dosage form.

Embodiment 21

A method of administering meloxicam orally, comprising orally administering a dosage form of embodiment 2, 3, 4, 5, 6, 7, 8, 9, 10, 11, 12, 13, 14, 15, 16, 17, 18, 19, or 20 to a patient in need of treatment.

Embodiment 22

The method of embodiment 21, wherein the dosage form is administered to treat pain.

Embodiment 23

The method of embodiment 21, wherein the dosage form is administered to treat inflammatory pain.

Embodiment 24

The method of embodiment 21, wherein the dosage form is administered to treat osteoarthritis, rheumatoid arthritis, or juvenile rheumatoid arthritis.

Embodiment 25

A method of administering meloxicam intravenously, comprising intravenously administering a dosage form of embodiment 2, 3, 4, 5, 6, 7, 8, 9, 10, 12, 13, 14, or 15, to a patient in need of treatment.

Example 1

The effect of varying amounts of potassium carbonate ($K_2CO_3$) and sodium bicarbonate ($NaHCO_3$) on the pH of acidic media was tested. The acidic media was chosen to simulate gastric conditions. $K_2CO_3$ or $NaHCO_3$ was added to 50 mL of a 0.01 N HCl solution (pH 2). The pH of the solution was measured after addition of the $K_2CO_3$ or $NaHCO3$. Deionized water (240 mL) was then added to the mixture and pH was measured again. The results are shown in Tables 1-4.

TABLE 1

Results with $K_2CO_3$ (0.01N HCl)

| $K_2CO_3$ (mg) | pH |
|---|---|
| 25 | 2.84 |
| 35 | 6.29 |
| 45 | 8.05 |
| 50 | 8.29 |
| 100 | 9.43 |
| 200 | 10.14 |
| 300 | 10.39 |
| 400 | 10.55 |
| 450 | 10.58 |

TABLE 2

Results with $K_2CO_3$ (0.01N HCl + Water)

| $K_2CO_3$ (mg) | pH |
|---|---|
| 200 | 10.27 |
| 300 | 10.46 |
| 400 | 10.57 |
| 450 | 10.63 |

TABLE 3

Results with $NaHCO_3$ (0.01N HCl)

| $NaHCO_3$ (mg) | pH |
|---|---|
| 200 | 5.28 |
| 300 | 5.90 |
| 400 | 6.44 |
| 450 | 6.86 |
| 500 | 8.23 |
| 750 | 8.30 |
| 1000 | 8.36 |

TABLE 4

Results with $NaHCO_3$ (0.01N HCl + Water)

| $NaHCO_3$ (mg) | pH |
|---|---|
| 200 | 5.41 |
| 300 | 5.89 |
| 400 | 6.11 |
| 450 | 6.46 |
| 500 | 8.33 |
| 750 | 8.54 |
| 1000 | 8.60 |

Example 2

Tablets containing meloxicam and combinations of cyclodextrin, $K_2CO3$, or $NaHCO_3$ were manufactured and tested for dissolution. Tablets containing meloxicam alone (MOBIC®) were purchased and also tested for dissolution. The tested tablets are listed in Table 5. Meloxicam in the form of meloxicam/cyclodextrin inclusion complexes was used in the tablets containing meloxicam and cyclodextrin. The inclusion complexes were formed by mixing meloxicam and cyclodextrin in an aqueous pH-adjusted solution. The pH of the solution was adjusted using buffering agents. The resulting soluble meloxicam/cyclodextrin inclusion complexes were then spray dried. This spray-dried dispersion was used in the manufacture of the tablets containing cyclodextrin.

TABLE 5

Tablets

| | |
|---|---|
| Tablet A | 15 mg meloxicam + 25 mg K₂CO3 |
| Tablet B | 15 mg meloxicam + 50 mg K₂CO3 |
| Tablet C | 15 mg meloxicam + 100 mg K₂CO3 |
| Tablet D | 15 mg meloxicam + 150 mg K₂CO3 |
| Tablet E | 15 mg meloxicam + 500 mg NaHCO3 |
| Tablet F | 15 mg meloxicam + 100 mg SBEβCD |
| Tablet G | 15 mg meloxicam + 100 mg SBEβCD + 25 mg K₂CO3 |
| Tablet H | 15 mg meloxicam + 100 mg SBEβCD + 50 mg K₂CO3 |
| Tablet I | 15 mg meloxicam + 100 mg SBEβCD + 100 mg K₂CO3 |
| Tablet J | 15 mg meloxicam + 100 mg SBEβCD + 150 mg K₂CO3 |
| Tablet K | 15 mg meloxicam + 100 mg SBEβCD + 500 mg NaHCO3 |
| Tablet L | 15 mg meloxicam (MOBIC ®) |

Dissolution testing in acidic medium (chosen to simulate gastric conditions) was performed by placing the tablets in a 0.01 N HCl solution, at an agitation rate of 75 RPM, and vessel temperature of approximately 37° C. The results are presented in Tables 6 and in FIGS. 1-10. Results at various time points (0, 15, 30, 45, 60, 90, and 120 minutes) are presented as percent (%) of meloxicam dissolved.

TABLE 6

Dissolution Results

| | 0 mins | 15 mins | 30 mins | 45 mins | 60 mins | 90 mins | 120 mins |
|---|---|---|---|---|---|---|---|
| Tablet A | 0% | 23% | 17% | 15% | 13% | 12% | 11% |
| Tablet B | 0% | 27% | 20% | 17% | 16% | 17% | 15% |
| Tablet C | 0% | 31% | 26% | 25% | 24% | 23% | 21% |
| Tablet D | 0% | 30% | 26% | 25% | 24% | 23% | 22% |
| Tablet E | 0% | 50% | 66% | 77% | 84% | 92% | 95% |
| Tablet F | 0% | 26% | 17% | 14% | 12% | 11% | 10% |
| Tablet G | 0% | 48% | 39% | 26% | 20% | 16% | 14% |
| Tablet H | 0% | 44% | 30% | 22% | 17% | 16% | 13% |
| Tablet I | 0% | 32% | 33% | 27% | 21% | 16% | 15% |
| Tablet J | 0% | 26% | 27% | 19% | 15% | 12% | 11% |
| Tablet K | 0% | 85% | 86% | 86% | 86% | 86% | 86% |
| Tablet L | 0% | 2% | 2% | 2% | 2% | 2% | 2% |

Dissolution of meloxicam was greater with the tablets containing various combinations of meloxicam and cyclodextrin, $K_2CO_3$, or $NaHCO_3$, as compared to tablets containing meloxicam alone. For example, after 120 minutes, dissolution of meloxicam tablets containing $NaHCO_3$ was 95% as compared to 2% for tablets containing meloxicam alone.

Dissolution of meloxicam increasing with increasing amounts of $K_2CO_3$ in the absence of cyclodextrin. However, in the presence of cyclodextrin, increasing amounts of $K_2CO_3$ did not appear to increase meloxicam dissolution. At the highest dose of potassium bicarbonate tested, meloxicam dissolution in the presence of cyclodextrin was reduced by approximately 50% as compared to meloxicam dissolution in the absence of cyclodextrin at 120 minutes.

Dissolution of meloxicam with $NaHCO_3$ was significantly greater than that observed with the highest dose of $K_2CO_3$ at 15 minutes (50% versus 30%), and at 120 minutes (92% versus 23%). Meloxicam dissolution in the presence of cyclodextrin was also significantly greater with $NaHCO_3$ as compared to the highest dose of $K_2CO_3$ at 15 minutes (85% versus 26%), and at 120 minutes (86% versus 12%). $NaHCO_3$ in the presence of cyclodextrin increased meloxicam dissolution at 15 minutes as compared to potassium bicarbonate which resulted in a reduction in dissolution.

Example 3

A bilayer tablet containing 1) an inclusion complex of SBEβCD with meloxicam, prepared as described below, and 2) sodium bicarbonate was prepared (SBEβCD-Meloxicam/Bicarbonate). The first layer contained an inclusion complex of 15 mg meloxicam and 100 mg SBEβCD, and 100 mg of sodium bicarbonate. The second layer contained 40 mg of esomeprazole and 400 mg of sodium bicarbonate.

A total of 20 human subjects were randomly assigned in a 1:1 ratio to treatment with the SBEβCD-Meloxicam/Bicarbonate tablets described above or Mobic® tablets (15 mg meloxicam), once daily for 6 days under fasting conditions.

Figure 11:
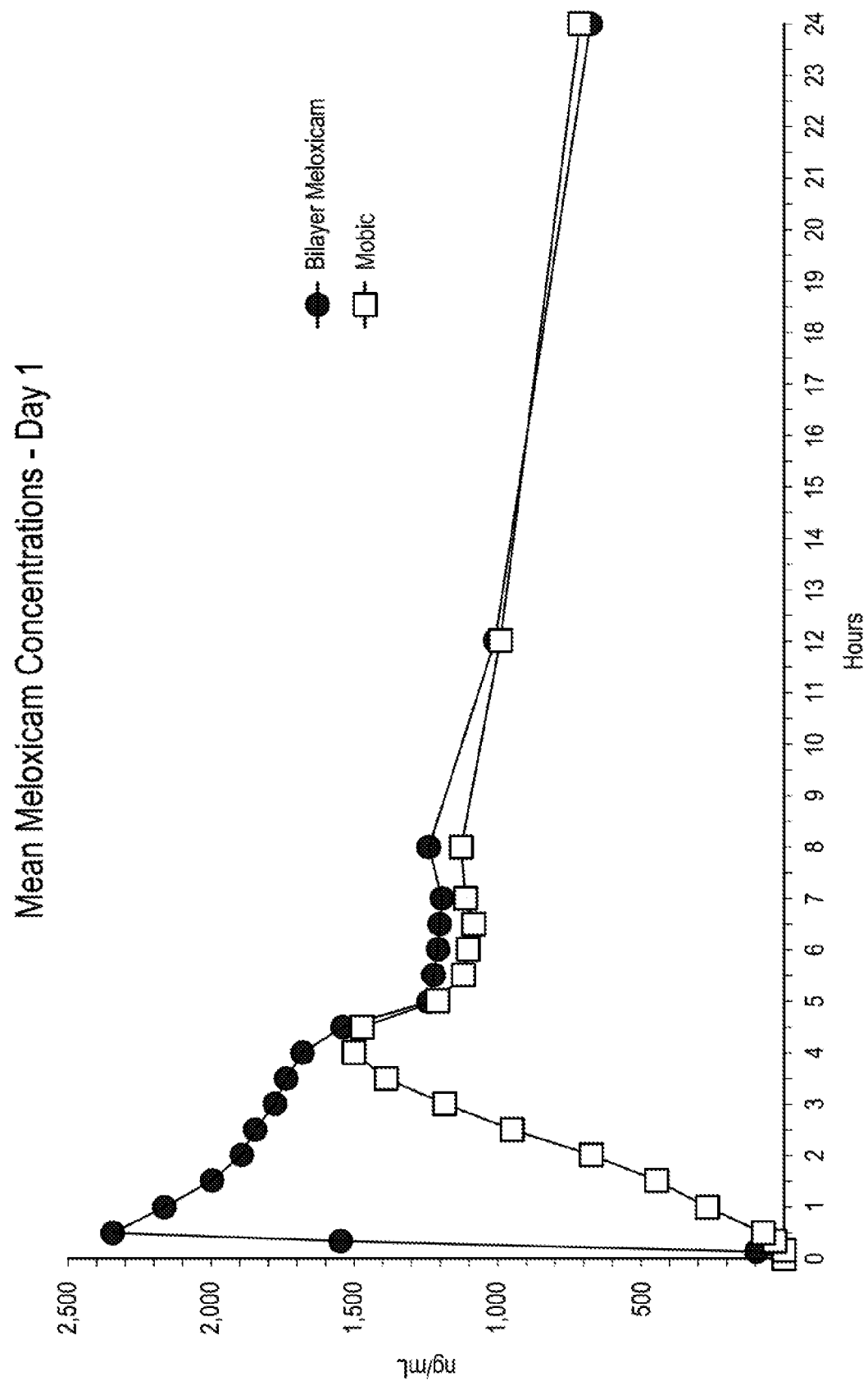
FIG. 11 is a plot of meloxicam plasma concentration at various time points over the first 24 hours for an embodiment of a dosage form described herein and a commercially available meloxicam dosage form.

On the first day of dosing, plasma samples were collected for concentration analysis of meloxicam at several time points. Concentrations of meloxicam were determined using LC-MS/MS. Pharmacokinetic parameters were calculated. The results are depicted in FIG. 11.

The median $T_{max}$ for meloxicam, the trial's primary endpoint, was 9 times faster for the SBEβCD-Meloxicam/Bicarbonate tablets as compared to Mobic® (0.5 hour versus 4.5 hours respectively, p<0.0001).

The SBEβCD-Meloxicam/Bicarbonate tablets also demonstrated higher mean maximum plasma concentration ($C_{max}$) (p=0.0018), faster time to therapeutic plasma concentration (p<0.0001), and faster time to half-maximal plasma concentration (p<0.0001) as compared to Mobic®.

Meloxicam in the form of meloxicam/cyclodextrin inclusion complexes was used in the tablets containing meloxicam and cyclodextrin. The inclusion complexes were formed by mixing meloxicam and cyclodextrin in an aqueous pH-adjusted solution. The pH of the solution was adjusted using buffering agents. The resulting soluble meloxicam/cyclodextrin inclusion complexes were then spray dried. This spray-dried dispersion was used in the manufacture of the tablets containing cyclodextrin.

Example 4

A monolayer tablet containing 1) the inclusion complex of SBEβCD with meloxicam; 2) rizatriptan; and 3) sodium bicarbonate was prepared (SBEβCD-Meloxicam/rizatriptan/Bicarbonate). The monolayer tablet contained 20 mg of meloxicam, 10 mg of rizatriptan, and 500 mg of sodium bicarbonate. The inclusion complex was the same as the inclusion complex of Example 3.

Dissolution testing of the tablets in acidic medium (chosen to simulate gastric conditions) was performed by placing the tablets in a 0.01 N HCl solution, at an agitation rate of 75 RPM, and vessel temperature of approximately 37° C. The results are presented in Table 7. Results at various time points (0, 15, 30, 45, 60, 90, and 120 minutes) are presented as percent (%) of meloxicam, and percent (%) of rizatriptan dissolved.

TABLE 7

| Dissolution Results | | | | | | | |
|---|---|---|---|---|---|---|---|
| Time-point (minutes) | 0 min | 15 min | 30 min | 45 min | 60 min | 90 min | 120 min |
| Rizatriptan | 0% | 89% | 102% | 103% | 103% | 103% | 103% |
| Meloxicam | 0% | 79% | 92% | 93% | 93% | 93% | 94% |

As shown in Table 7, the dissolution results of the tablets in Example 4 are very similar to the dissolution result of Example 3. Therefore, we expect the pharmacokinetic properties, including bioavailability, $T_{max}$, etc., of the tablets in Example 4 to be similar to those described in Example 3 and FIG. 11.

Example 5

The monolayer tablet of Example 4 was administered to six human subjects. On the first day of dosing, plasma samples were collected for concentration analysis of rizatriptan at several time points. Concentrations of rizatriptan and meloxicam were determined using LC-MS/MS. Pharmacokinetic parameters were calculated. The results for meloxicam were comparable to those reported for the bilayer dosage form of Example 3. The median $T_{max}$ of rizatriptan was 0.75 hours and the mean $C_{max}$ of rizatriptan was 20.710 ng/mL. By comparison, the reported $T_{max}$ of the commercial rizatriptan dosage form, Maxalt®, is 1.0-1.5 hours.

Unless otherwise indicated, all numbers expressing quantities of ingredients, properties such as molecular weight, reaction conditions, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A method of treating migraine comprising: selecting a human migraine patient with a history of inadequate response to prior migraine treatments, and orally administering a dosage form to the migraine patient, wherein the dosage form comprises a combination of: 1) a complex of meloxicam with a sulfobutyl ether β-cyclodextrin (SBEβCD), 2) a bicarbonate, and 3) a rizatriptan, wherein the human migraine patient is free of nausea two hours after the dosage form is orally administered to the human migraine patient.

2. The method of claim 1, wherein the oral dosage form contains 400 mg to 600 mg of the bicarbonate.

3. The method of claim 1, wherein the oral dosage form contains about 5 mg to about 50 mg of meloxicam.

4. The method of claim 1, wherein the oral dosage form contains about 50 mg to about 200 mg of the SBEβCD.

5. The method of claim 1, wherein the dosage form is a solid oral dosage form having a shorter $T_{max}$ of meloxicam in the human migraine patient than a reference dosage form that: 1) contains the same amount of meloxicam, 2) does not contain an SBEβCD, and 3) does not contain a bicarbonate.

6. The method of claim 5, wherein the solid oral dosage form has been shown to have faster time to therapeutic plasma concentration in the human migraine patient as compared to the reference dosage form.

7. The method of claim 1, wherein about 1 mg to about 50 mg of the rizatriptan is present in the oral dosage form based upon the weight of the rizatriptan in the free base form.

8. The method of claim 1, wherein the rizatriptan is present in a salt form in an amount that is a molar equivalent of about 10 mg of the rizatriptan in the free base form.

9. The method of claim 1, wherein the rizatriptan is present as rizatriptan benzoate.

10. The method of claim 1, wherein the oral dosage form contains about 10 mg to about 30 mg of meloxicam.

11. The method of claim 1, wherein the oral dosage form contains about 20 mg of meloxicam.

12. The method of claim 1, wherein the oral dosage form contains about 15 mg of meloxicam.

13. The method of claim 1, wherein the SBEβCD has about 6 to about 7 sulfobutyl ether groups for each molecule of β-cyclodextrin.

14. The method of claim 1, wherein the oral dosage form contains about 50 mg to about 150 mg of the SBEβCD.

15. The method of claim 1, wherein the oral dosage form contains about 100 mg of the SBEβCD.

16. The method of claim 1, wherein the molar ratio of the SBEβCD to meloxicam is about 0.5 to about 2.

17. The method of claim 1, wherein the molar ratio of the SBEβCD to meloxicam is about 0.8 to about 1.2.

18. The method of claim 1, wherein the molar ratio of the SBEβCD to meloxicam is about 1.

19. The method of claim 1, wherein the oral dosage form contains about 10 mg to about 40 mg of meloxicam, and about 5 mg to about 50 mg of the rizatriptan.

20. The method of claim 1, wherein the oral dosage form contains the SBEβCD that is in a weight ratio to the rizatriptan that is within a range of about 1 to about 100.

21. The method of claim 1, wherein the oral dosage form contains the SBEβCD that is in a weight ratio to the rizatriptan that is about 10.

22. The method of claim 1, wherein the bicarbonate comprises sodium bicarbonate.

23. The method of claim 1, wherein the oral dosage form contains 500 mg of sodium bicarbonate.

24. The method of claim 1, wherein the oral dosage form has been shown to have a median $T_{max}$ of meloxicam that is less than about 90 minutes in fasted human subjects.

25. The method of claim 1, wherein the oral dosage form has been shown to have a median $T_{max}$ of meloxicam that is less than about 2 hours in fasted human subjects.

* * * * *